US009233927B2

(12) United States Patent
Frenkel et al.

(10) Patent No.: US 9,233,927 B2
(45) Date of Patent: Jan. 12, 2016

(54) CRYSTALS OF LAQUINIMOD SODIUM AND IMPROVED PROCESS FOR THE MANUFACTURE THEREOF

(71) Applicants: Anton Frenkel, Netanya (IL); Avital Laxer, Tel Aviv (IL)

(72) Inventors: Anton Frenkel, Netanya (IL); Avital Laxer, Tel Aviv (IL)

(73) Assignee: TEVA PHARMACEUTICAL INDUSTRIES, LTD., Petach-Tikva (IL)

( * ) Notice: Subject to any disclaimer, the term of this patent is extended or adjusted under 35 U.S.C. 154(b) by 0 days.

(21) Appl. No.: 14/214,191

(22) Filed: Mar. 14, 2014

(65) Prior Publication Data
US 2014/0271878 A1    Sep. 18, 2014

Related U.S. Application Data

(60) Provisional application No. 61/785,575, filed on Mar. 14, 2013.

(51) Int. Cl.
C07D 215/56    (2006.01)

(52) U.S. Cl.
CPC .................. C07D 215/56 (2013.01)

(58) Field of Classification Search
CPC .................................... C07D 215/56
USPC ......................................... 546/156
See application file for complete search history.

(56) References Cited

U.S. PATENT DOCUMENTS

| | | | |
|---|---|---|---|
| 3,024,257 A | 3/1962 | Millar at al. |
| 4,107,310 A | 8/1978 | Allais et al. |
| 4,547,511 A | 10/1985 | Eriksoo et al. |
| 4,628,053 A | 12/1986 | Fries et al. |
| 4,738,971 A | 4/1988 | Eriksoo et al. |
| 4,782,155 A | 11/1988 | Nakagawa et al. |
| 5,139,878 A | 8/1992 | Kim et al. |
| 5,710,638 A | 1/1998 | Touitou et al. |
| 5,912,349 A | 6/1999 | Sih |
| 6,077,851 A | 6/2000 | Bjork et al. |
| 6,121,287 A | 9/2000 | Bjork et al. |
| 6,133,285 A | 10/2000 | Bjork et al. |
| 6,307,050 B1 | 10/2001 | Kwiatkowski et al. |
| 6,395,750 B1 | 5/2002 | Hellund et al. |
| 6,593,343 B2 | 7/2003 | Bjork et al. |
| 6,605,616 B1 | 8/2003 | Bjork et al. |
| 6,613,574 B2 | 9/2003 | Shimada |
| 6,706,733 B2 | 3/2004 | Kimura et al. |
| 6,802,422 B2 | 10/2004 | Kavelage et al. |
| 6,875,869 B2 | 4/2005 | Jansson |
| 7,560,557 B2 | 7/2009 | Jansson |
| 7,589,208 B2 | 9/2009 | Jansson et al. |
| 7,790,197 B2 | 9/2010 | Fergione et al. |
| 7,884,208 B2* | 2/2011 | Frenkel et al. ........ 546/156 |
| 7,989,473 B2 | 8/2011 | Patashnik et al. |
| 8,178,127 B2 | 5/2012 | Safadi et al. |
| 8,252,933 B2 | 8/2012 | Gant et al. |
| 8,314,124 B2 | 11/2012 | Jansson et al. |
| 8,383,645 B2 | 2/2013 | Patashnik et al. |
| 8,545,885 B2 | 10/2013 | Safadi et al. |
| 8,598,203 B2 | 12/2013 | Tarcic et al. |
| 8,647,646 B2 | 2/2014 | Frenkel et al. |
| 8,673,322 B2 | 3/2014 | Frenkel et al. |
| 2002/0173520 A1 | 11/2002 | Bjork et al. |
| 2003/0119826 A1 | 6/2003 | Manning et al. |
| 2003/0124187 A1 | 7/2003 | Mention et al. |
| 2004/0253305 A1 | 12/2004 | Luner et al. |

(Continued)

FOREIGN PATENT DOCUMENTS

EP    0497740    12/1994
EP    1073639    11/2002

(Continued)

OTHER PUBLICATIONS

PCT International Search Report issued Apr. 26, 2007 in connection with PCT International Application No. PCT/US2006/040925.
Written Opinion of the International Searching Authority issued Apr. 26, 2007 in connection with PCT International Application No. PCT/US2006/040925.
PCT International Preliminary Report on Patentability issued Apr. 23, 2008 in connection with PCT International Application No. PCT/US2006/040925.

(Continued)

*Primary Examiner* — D Margaret M. Seaman
(74) *Attorney, Agent, or Firm* — John P. White; Gary J. Gershik; Cooper & Dunham LLP

(57) ABSTRACT

The subject invention provides a mixture of crystalline laquinimod sodium particles, wherein (i) 90% or more of the total amount by volume of the laquinimod sodium particles have a size of 40 microns or less or (ii) 50% or more of the total amount by volume of the laquinimod sodium particles have a size of 15 microns or less, and wherein:

a) the mixture has a bulk density of 0.2 g/mL to 0.4 g/mL;

b) the mixture has a tapped density of 0.40 g/mL to 0.7 g/mL;

c) an amount of heavy metal in the mixture is no more than 0.002% of heavy metal relative to the amount by weight of laquinimod sodium;

d) an amount of 5-chloro-4-hydroxy-1-methyl-2-oxo-1,2-dihydroquinoline (MCQ) in the mixture is no more than 0.15% relative to the amount of laquinimod sodium as measured by HPLC;

e) an amount of 5-chloro-4-hydroxy-1-methyl-2-oxo-1,2-dihydroqunoline-3-carboxylic acid (MCQCA) in the mixture is no more than 0.15% relative to the amount of laquinimod sodium as measured by HPLC; or f) an amount of methyl 5-chloro-4-hydroxy-1-methyl-2-oxo-1,2-dihydroquinoline-3-carboxylate (MCQME) in the mixture is no more than 0.12% relative to the amount of laquinimod sodium as measured by HPLC.

22 Claims, 8 Drawing Sheets

(56) References Cited

U.S. PATENT DOCUMENTS

| | | |
|---|---|---|
| 2005/0192315 A1 | 9/2005 | Jansson et al. |
| 2005/0215586 A1 | 9/2005 | Jansson et al. |
| 2005/0271717 A1 | 12/2005 | Berchielli et al. |
| 2007/0218062 A1 | 9/2007 | Irving |
| 2007/0280891 A1 | 12/2007 | Tamarkin et al. |
| 2010/0158903 A1 | 6/2010 | Smith et al. |
| 2010/0209506 A1 | 8/2010 | Eisenreich |
| 2010/0260716 A1 | 10/2010 | Stohr et al. |
| 2010/0260755 A1 | 10/2010 | Gammans et al. |
| 2010/0310547 A1 | 12/2010 | Soliven |
| 2010/0322900 A1 | 12/2010 | Tarcic et al. |
| 2011/0034508 A1 | 2/2011 | Hayardeny |
| 2011/0171270 A1 | 7/2011 | Dixit et al. |
| 2011/0217295 A1 | 9/2011 | Haviv et al. |
| 2011/0218179 A1 | 9/2011 | Haviv et al. |
| 2011/0218203 A1 | 9/2011 | Kaye et al. |
| 2011/0251235 A1 | 10/2011 | Patashnik et al. |
| 2012/0010238 A1 | 1/2012 | Piryatinsky |
| 2012/0010239 A1 | 1/2012 | Fristedt |
| 2012/0142730 A1 | 6/2012 | Tarcic et al. |
| 2012/0142748 A1 | 6/2012 | Muthuppalaniappan et al. |
| 2013/0028866 A1 | 1/2013 | Gilgun et al. |
| 2013/0029916 A1 | 1/2013 | Gilgun et al. |
| 2013/0096158 A1 | 4/2013 | Hallak et al. |
| 2013/0184310 A1 | 7/2013 | Haviv et al. |
| 2013/0203807 A1 | 8/2013 | Tarcic et al. |
| 2013/0217724 A1 | 8/2013 | Ioffe et al. |
| 2013/0259856 A1 | 10/2013 | Kaye |
| 2013/0272996 A1 | 10/2013 | Tarcic et al. |
| 2013/0303569 A1 | 11/2013 | Bar-Zohar et al. |
| 2013/0345256 A1 | 12/2013 | Laxer et al. |
| 2013/0345257 A1 | 12/2013 | Hahn et al. |
| 2014/0017226 A1 | 1/2014 | Kaye et al. |
| 2014/0018386 A1 | 1/2014 | Sarfati et al. |
| 2014/0024678 A1 | 1/2014 | Sadafi et al |
| 2014/0045886 A1 | 2/2014 | Martino et al. |
| 2014/0045887 A1 | 2/2014 | Martino et al. |

FOREIGN PATENT DOCUMENTS

| | | |
|---|---|---|
| EP | 1097139 | 12/2002 |
| EP | 1095021 | 9/2003 |
| EP | 1511732 | 12/2006 |
| EP | 1720531 | 4/2011 |
| WO | WO 90/15052 | 12/1990 |
| WO | WO 99/15052 | 1/1999 |
| WO | WO 99/55678 | 11/1999 |
| WO | WO 00/03991 | 1/2000 |
| WO | WO 00/03992 | 1/2000 |
| WO | WO 01/30758 | 5/2001 |
| WO | WO 02/18343 | 3/2002 |
| WO | WO 03/106424 | 12/2003 |
| WO | WO 2004/013153 | 2/2004 |
| WO | WO 2005/074899 | 8/2005 |
| WO | WO 2012/069202 | 5/2012 |
| WO | WO 2012/175541 | 12/2012 |
| WO | WO 2012/169746 | 11/2013 |

OTHER PUBLICATIONS

PCT international Search Report issued Feb. 20, 2009 in connection with PCT International Application No. PCT/US2008/13890.

Written Opinion of the International Searching Authority issued Mar. 10, 2014 in connection with PCT International Application No. PCT/US13/67686.

\* cited by examiner

System Suitability Separation Results

| | Name | RT | RT Ratio | Area | USP Resolution | USP Tailing | Int Type |
|---|---|---|---|---|---|---|---|
| 1 | MCQME | 5.480 | 0.36 | 35801 | | 1.07 | BB |
| 2 | MCQ | 8.260 | 0.54 | 60697 | 8.2 | 1.16 | BV |
| 3 | MCQEE | 9.249 | 0.80 | 24329 | 2.6 | 1.05 | VB |
| 4 | MCQCA | 12.031 | 0.78 | 18609 | 5.7 | 1.34 | BB |
| 5 | Laquinimod | 15.332 | | 12332469 | 5.2 | 1.64 | BB |
| 6 | 5-HLAQ | 20.451 | 1.33 | 80463 | 7.3 | 1.04 | BB |

CRYSTALS OF LAQUINIMOD SODIUM AND IMPROVED PROCESS FOR THE MANUFACTURE THEREOF

This application claims benefit of U.S. Provisional Application No. 61/785,575, filed Mar. 14, 2013, the entire content of which is hereby incorporated by reference herein.

Throughout this application, various publications are referred to by first author and year of publication. Full citations for these publications are presented in a References section immediately before the claims. Disclosures of the publications cited in the References section in their entireties are hereby incorporated by reference into this application in order to more fully describe the state of the art as of the date of the invention described herein.

BACKGROUND OF THE INVENTION

Laquinimod is a compound which has been shown to be effective in the acute experimental autoimmune encephalomyelitis (aEAE) model (U.S. Pat. No. 6,077,851). Its chemical name is N-ethyl-N-phenyl-1,2,-dihydro-4-hydroxy-5-chloro-1-methyl-2-oxoquinoline-3-carboxamide, and its Chemical Registry number is 248281-84-7.

Laquinimod is a small, molecule having the following chemical structure:

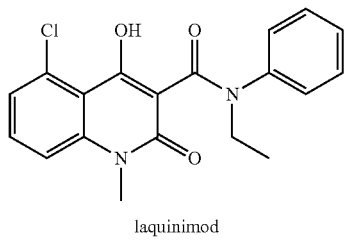 [SMILES: CCN(C(=O)c1c(O)c2c(Cl)cccc2n(C)c1=O)c1ccccc1]

laquinimod

The processes of synthesis of laquinimod and the preparation of its sodium salt are disclosed in U.S. Pat. No. 6,077,851. An additional process of synthesis of laquinimod acid, but not laquinimod sodium, having low levels of impurities disclosed in U.S. Pat. No. 6,875,869. U.S. Pat. No. 7,894,208 teaches a process for the preparation of laquinimod sodium which removes the impurities present after the salt formation step, thus resulting in a crystalline mixture of higher purity as well as a crystalline mixture having large particles, and good tapped and bulk density. Pharmaceutical compositions comprising laquinimod sodium are disclosed in PCT International Application Publication No. WO 2005/074899.

In the preparation of laquinimod sodium disclosed in U.S. Pat. No. 6,077,851, laquinimod acid was suspended in ethanol, and 5M sodium hydroxide solution was added. After stirring, the resulting precipitate was filtered, washed with ethanol, and dried. The method used to make laquinimod sodium in U.S. Pat. No. 6,077,851 is commonly referred to as a slurry-to-slurry salt formation.

In the slurry-to-slurry salt formation method of U.S. Pat. No. 6,077,851, the laquinimod sodium is not dissolved in solution. Any solid impurities, if present in the laquinimod sodium suspension, are therefore not removed by filtration.

U.S. Pat. No. 6,875,869 discloses a process of preparing the base compound laquinimod in high yield and low level of impurities. However, the process in U.S. Pat. No. 6,875,869 is only for synthesis of the base compound (lauqinimod acid) and not the salt. As such, the slurry-to-slurry salt formation process would still be needed to form the sodium salt.

U.S. Pat. No. 7,884,208 teaches an improved process for preparing laquinimod sodium resulting in crystals of higher purity as well as crystals having improved crystalline characteristics, e.g., comprising no more than 2 ppm of a heavy metal and having higher tapped density. In the process disclosed in U.S. Pat. No. 7,884,208 in Examples 13-17, laquinimod sodium is dissolved in water to form an aqueous solution; the aqueous solution is concentrated; and then a water-miscible anti-solvent is added to the concentrated solution to form laquinimod sodium crystals. The process of U.S. Pat. No. 7,884,208 removes the impurities after salt formation, thus resulting in laquinimod sodium of higher purity than the laquinimod sodium produced directly from the "slurry to slurry" process of U.S. Pat. No. 6,077,851.

SUMMARY OF THE INVENTION

The subject invention provides a mixture of crystalline laquinimod sodium particles, wherein (i) 90% or more of the total amount by volume of the laquinimod sodium particles have a size of 40 microns or less or (ii) 50% or more of the total amount by volume of the laquinimod sodium particles have a size of 15 microns or less, and wherein:
  a) the has a bulk density of 0.2 q/mL to 0.4 g/mL;
  b) the mixture has a tapped density of 0.40 g/mL to 0.7 g/mL;
  c) an amount of heavy metal in the mixture is no more than 0.002% of heavy metal relative to the amount by weight of laquinimod sodium;
  d) an amount of 5-chloro-4-hydroxy-1-methyl-2-oxo-1,2-dihydroqunoline (MCQ) in the mixture is no more than 0.15% relative to the amount of laquinimod sodium as measured by HPLC;
  e) an amount of 5-chloro-4-hydroxyl-2-oxo-2-dihydro-quinoline-3-carboxylic acid (MCQCA) in the mixture is no more than 0.15% relative to the amount of laquinimod sodium as measured by HPLC; or
  f) an amount of methyl 5-chloro-4-hydroxy-1-methyl-2-oxo-1,2-dihydroquinoline-3-carboxylate (MCQME) in the mixture is no more than 0.12% relative to the amount of laquinimod sodium as measured by HPLC.

The subject invention provides a mixture of crystalline laquinimod sodium particles, wherein (i) 90% or more of the total amount by volume of the laquinimod sodium particles have a size of less than 40 microns, (ii) 50% or more of the total amount by volume of the laquinimod sodium particles have a size of less than 15 microns, and (iii) 10% or more of the total amount by volume of the laquinimod sodium particles have a size of less than 5 microns and wherein:
  a) the mixture has a bulk density of 0.2 g/mL to 0.4 g/mL;
  b) the mixture has a tapped density of 0.40 g/mL to 0.7 g/mL;
  c) an amount of heavy metal in the mixture is no more than 0.002% of heavy metal relative to the amount by weight of laquinimod sodium;
  d) en amount of 5-chloro-4-hydroxy-1-methyl-2-oxo-1,2-dihydroquinoline (MCQ) in the mixture is no more than 0.15% relative to the amount of laquinimod sodium as measured by HPLC;
  e) an amount of 5-chloro-4-hydroxy-1-methyl-2-oxo-1,2-dihydroquinoline-3-carboxylic acid (MCQCA) in the mixture is no more than 0.15% relative to the amount of laquinimod sodium as measured by HPLC; or
  f) an amount of methyl 5-chloro-4-hydroxy-1-methyl-2-oxo-1,2-dihydroquinoline-3-carboxylate (MCQME) in the mixture is no more than 0.12% relative to the amount of laquinimod sodium as measured by HPLC.

The subject invention provides a process of recrystallization of laquinimod sodium comprising:
- a) dissolving an amount of laquinimod sodium in water to form an aqueous solution;
- b) concentrating the aqueous solution to form a concentrated solution comprising approximately 1.7-1.8 mL of water per gram of laquinimod sodium;
- c) adding acetone to the concentrated solution of step b); and
- d) isolating recrystallized laquinimod sodium.

The subject invention provides a mixture of crystalline laquinimod sodium particles, wherein (i) 90% or more of the total amount by volume of the laquinimod sodium particles have a size of 40 microns or less or (ii) 50% or more of the total amount by volume of the laquinimod sodium particles have a size of 15 microns or less, and wherein
- a) an amount of aluminium in the mixture is less than 5 ppm relative to the amount by weight of laquinimod sodium;
- b) an amount of calcium in the mixture is less than 60 ppm relative to the amount by weight of laquinimod sodium;
- c) an amount of copper in the mixture is less than 1 ppm relative to the amount by weight of laquinimod sodium;
- d) an amount of iron in the mixture is less than 4 ppm relative to the amount by weight of laquinimod sodium; or
- e) an amount of zinc in the mixture is less than 7 ppm relative to the amount by weight of laquinimod sodium.

BRIEF DESCRIPTION OF FIGURES

FIG. 1 from U.S. Pat. No. 7,884,208.
FIG. 2 from U.S. Pat. No. 7,884,208.

DETAILED DESCRIPTION OF THE INVENTION

Figure 1:
FIG. 1.
Figure 2:
FIG. 2.
Figure 3:
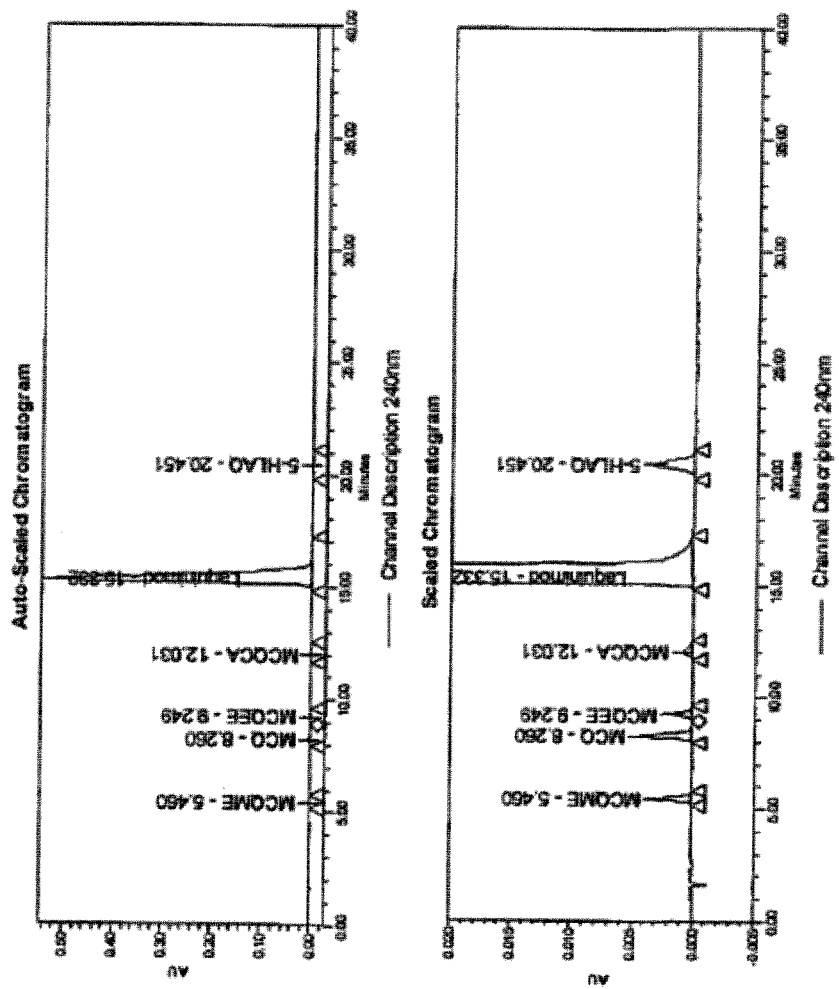
FIG. 3: HPLC Data—Example chromatogram of mixture of Laquinimod sodium.
Figures 3, 4:
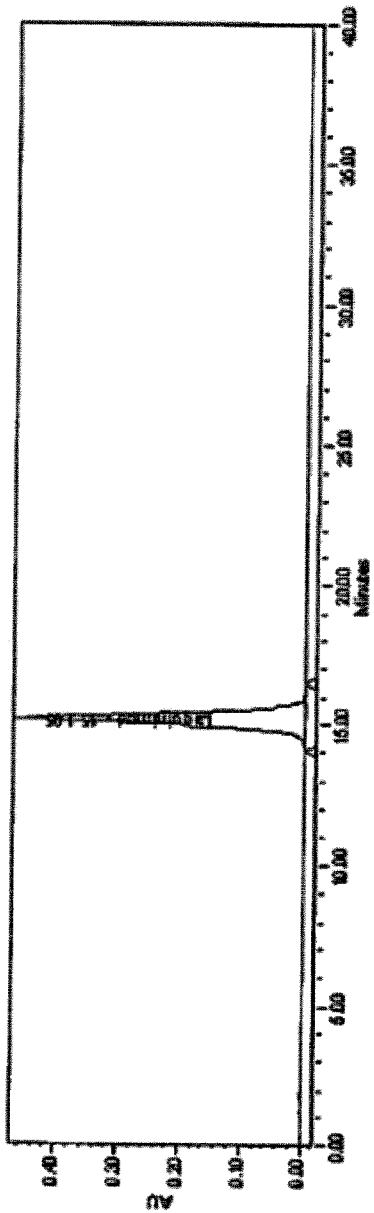
FIG. 4: HPLC Data—Pure chromatogram of Laquinimod Sodium.

The subject invention provides a mixture of crystalline laquinimod sodium particles, wherein (i) 90% or more of the total amount by volume of the laquinimod sodium particles have a size of 40 microns or less or (ii) 50% or more of the total amount by volume of the laquinimod sodium particles have a size of 15 microns or less, and wherein:
- a) the mixture has a bulk density of 0.2 g/mL to 0.4 g/mL;
- b) the mixture has a tapped density of 0.40 g/mL to 0.7 g/mL;
- c) an amount of heavy metal in the mixture is no more than 0.002% of heavy metal relative to the amount by weight of laquinimod sodium;
- d) an amount of 5-chloro-4-hydroxy-1-methyl-2-oxo-1,2-dihydroquinoline (MCQ) in the mixture is no more than 0.15% relative to the amount of laquinimod sodium as measured by HPLC;
- e) an amount of 5-chloro-4-hydroxy-1-methyl-2-oxo-1,2-dihydroquinoline-3-carboxylic acid (MCQCA) in the mixture is no more than 0.15% relative to the amount of laquinimod sodium as measured by HPLC; or
- f) an amount of methyl 5-chloro-4-hydroxy-1-methyl-2-oxo-1,2-dihydroquinoline-3-carboxylate (MCQME) in the mixture is no more than 0.12% relative to the amount of laquinimod sodium as measured by HPLC.

In an embodiment of the mixture, (i) 90% or more of the total amount by volume of the laquinimod sodium particles have a size of less than 40 microns or (ii) 50% or more of the total amount by volume of the laquinimod sodium particles have a size of less than 15 microns.

In an embodiment of the mixture, 10% or more of the total amount by volume of the laquinimod sodium particles have a size of 5 microns or less and wherein:
- a) the mixture has a tapped density of 0.40 g/mL to 0.7 g/mL; or
- b) an amount of 5-chloro-4-hydroxy-1-methyl-2-oxo-1,2-dihydroquinoline (MCQ) in the mixture is no more than 0.15% relative to the amount of laquinimod sodium as measured by HPLC.

The subject invention provides a mixture of crystalline laquinimod sodium particles, wherein (i) 90% or more of the total amount by volume of the laquinimod sodium particles have a size of less than 40 microns, (ii) 50% or more of the total amount by volume of the laquinimod sodium particles have a size of less than 15 microns, and (iii) 10% or more of the total amount by volume of the laquinimod sodium particles have a size of less than 5 microns and wherein:
- a) the mixture has a bulk density of 0.2 g/mL to 0.4 g/mL;
- b) the mixture has a tapped density of 0.40 g/mL to 0.7 g/mL;
- c) an amount of heavy metal in the mixture is no more than 0.002% of heavy metal relative to the amount by weight of laquinimod sodium;
- d) an amount of 5-chloro-4-hydroxy-1-methyl-2-oxo-1,2-dihydroquinoline (MCQ) in the mixture is no more than 0.15% relative to the amount of laquinimod sodium as measured by HPLC;
- e) an amount of 5-chloro-4-hydroxy-1-methyl-2-oxo-1,2-dihydroquinoline-3-carboxylic acid (MCQCA) in the mixture is no more than 0.15% relative to the amount of laquinimod sodium as measured by HPLC;
- f) an amount of methyl 5-chloro-4-hydroxy-1-methyl-2-oxo-1,2-dihydroquinoline-3-carboxylate (MCQME) in the mixture is no more than 0.12% relative to the amount of laquinimod sodium as measured by HPLC.

In an embodiment of the mixture, the mixture is prepared in a single batch comprising 2.5 kg or more of laquinimod sodium.

In an embodiment of the mixture, the laquinimod sodium particles are determined based on an unmilled sample of the mixture.

In an embodiment of the mixture, the size and amount by volume of laquinimod sodium particles are determined based on a milled sample of the mixture.

In an embodiment of the mixture, the mixture has a bulk density of 0.2 g/mL to 0.4 g/mL.

In an embodiment of the mixture, the mixture has a tapped density of 0.40 g/mL to 0.7 g/mL.

In an embodiment of the mixture, an amount of aluminium in the mixture is less than 5 ppm relative to the amount by weight of laquinimod sodium.

In an embodiment of the mixture, an amount of aluminium in the mixture is less than 2 ppm relative to the amount by weight of laquinimod sodium.

In an embodiment of the mixture, an amount of calcium in the mixture is less than 60 ppm relative to the amount by weight of laquinimod sodium.

In an embodiment of the mixture, an amount of calcium in the mixture is less than 25 ppm relative to the amount by weight of laquinimod sodium.

In an embodiment of the mixture, an amount of copper in the mixture is less than 1 ppm relative to the amount by weight of laquinimod sodium.

In an embodiment of the mixture, an amount of copper in the mixture is less than 0.6 ppm relative to the amount by weight of laquinimod sodium.

In an embodiment of the mixture, an amount of iron in the mixture is less than 4 ppm relative to the amount by weight of laquinimod sodium.

In an embodiment of the mixture, an amount of iron in the mixture is less than 3.6 ppm relative to the amount by weight of laquinimod sodium.

In an embodiment of the mixture, an amount of zinc in the mixture is less than 7 ppm relative to the amount by weight of laquinimod sodium.

In an embodiment of the mixture, an amount of zinc in the mixture is less than 4 ppm relative to the amount by weight of laquinimod sodium.

In an embodiment of the mixture, an amount of heavy metal in the mixture is no more than 20 ppm relative to the amount by weight of laquinimod sodium.

In an embodiment of the mixture, an amount of heavy metal in the mixture is no more than 2 ppm relative to the amount by weight of laquinimod sodium.

In an embodiment of the mixture, a total amount of polar impurities in the mixture is no more than 1.00% relative to the amount of laquinimod sodium as measured by HPLC.

In an embodiment of the mixture, an amount of 5-chloro-4-hydroxy-1-methyl-2-oxo-1,2-dihydroquinoline (MCQ) in the mixture is no more than 0.15% relative to the amount of laquinimod sodium as measured by HPLC.

In an embodiment of the mixture, an amount of 5-chloro-4-hydroxy-1-methyl-2-oxo-1,2-dihydroquinoline-3-carboxylic acid (MCQCA) in the mixture is no more than 0.15% relative to the amount of laquinimod sodium as measured by HPLC.

In an embodiment of the mixture, an amount of methyl 5-chloro-4-hydroxy-1-methyl-2-oxo-1,2-dihydroquinoline-3-carboxylate (MCQME) in the mixture is no more than 0.12% relative to the amount of laquinimod sodium as measured by HPLC.

In an embodiment of the mixture, an amount of ethyl 5-chloro-4-hydroxy-1-methyl-2-oxo-1,2-dihydroquinoline-3-carboxylate (MCQEE) in the mixture is no more than 0.10% relative to the amount of laquinimod sodium as measured by HPLC.

In an embodiment of the mixture, a total amount of non-polar impurities in the mixture is no more than 0.50% relative to the amount of laquinimod sodium as measured by HPLC.

In an embodiment of the mixture, an amount of N-ethyl aniline in the mixture is no more than 0.10% relative to the amount of laquinimod sodium as measured by HPLC.

In an embodiment of the mixture, an amount of N-ethyl-4,5-dihydroxy-1-methyl-2-oxo-N-phenyl-1,2,3,4-tetrahydroquinoline-3-carboxamide (5-HLAQ) in the mixture is no more than 0.10% relative to the amount of laquinimod sodium as measured by HPLC.

In an embodiment of the mixture, an amount of 5-chloro-4-hydroxy-1-methyl-2-oxo-N-phenyl-1,2-dihydroquinoline-3-carboxamide (DELAQ) in the mixture is no more than 0.10% relative to the amount of laquinimod sodium as measured by HPLC.

In an embodiment of the mixture, an amount of laquinimod acid in the mixture is no more than 1.00% relative to the amount of laquinimod sodium as measured by HPLC.

In an embodiment of the mixture, an amount of dimethyl malonate in the mixture is no more than 0.10% relative to the amount of laquinimod sodium as measured by HPLC.

In an embodiment of the mixture, an amount of diethyl malonate in the mixture is no more than 0.10% relative to the amount of laquinimod sodium as measured by HPLC.

In an embodiment of the mixture, an amount of dimethyl sulfate in the mixture is no more than 1 ppm relative to the amount by weight of laquinimod sodium.

In an embodiment of the mixture, an amount of water in the mixture is no more than 1.5% by weight relative to the amount of laquinimod sodium as measured by K.F. coulometric titration.

In an embodiment of the mixture, an amount of sodium from 5.8% to 6.4% relative to the amount by weight of laquinimod sodium.

In an embodiment of the mixture, an amount of ethanol in the mixture is no more than 5000 ppm relative to the amount by weight of laquinimod sodium.

In an embodiment of the mixture, an amount of n-heptane in the mixture is no more than 5000 ppm relative to the amount by weight of laquinimod sodium.

In an embodiment of the mixture, an amount of n-heptane in the mixture is no more than 2000 ppm n-octane relative to the amount by weight of laquinimod sodium.

In an embodiment of the mixture, an amount of methanol in the mixture is no more than 3000 ppm relative to the amount by weight of laquinimod sodium.

In an embodiment of the mixture, an amount of acetone in the mixture is no more than 5000 ppm relative to the amount by weight of laquinimod sodium.

In an embodiment of the mixture, an amount of dioxane in the mixture is no more than 380 ppm relative to the amount by weight of laquinimod sodium.

In an embodiment of the mixture, an amount of dimethyl formamide in the mixture is no more than 880 ppm relative to the amount by weight of laquinimod sodium.

The subject invention provides a pharmaceutical composition comprising the mixture of the subject invention and a pharmaceutically acceptable carrier.

In an embodiment of the pharmaceutical composition, a total amount of 5-chloro-4-hydroxy-1-methyl-2-oxo-1,2-dihydroquinoline (MCQ) and 5-chloro-4-hydroxy-1-methyl-2-oxo-1,2-dihydroquinoline-3-carboxylic acid (MCQCA) in the pharmaceutical composition is no more than 0.50% relative to the amount of laquinimod sodium as measured by HPLC.

In an embodiment of the pharmaceutical composition, a total amount of polar impurities in the pharmaceutical composition is no more than 2.001 relative to the amount of laquinimod sodium as measured by HPLC.

In an embodiment of the pharmaceutical composition, an amount of N-ethyl aniline in the pharmaceutical composition is no more than 0.50% relative to the amount of laquinimod sodium as measured by HPLC.

In an embodiment of the pharmaceutical composition, an amount of 5-chloro-N-ethyl-3-hydroxy-1-methyl-5-2,4-dioxo-N-phenyl-1,2,3,4-tetrahydroquinoline-3-carboxamide (3-HLAQ) in the pharmaceutical composition is no more than 0.50% relative to the amount of laquinimod sodium as measured by HPLC.

In an embodiment of the pharmaceutical composition, a total amount of non-polar impurities in the pharmaceutical composition is no more than 1.00% relative to the amount of laquinimod sodium as measured by HPLC.

In an embodiment of the pharmaceutical composition, an amount of N-ethyl-4-hydroxy-1-methyl-5-(methyl(2,3,4,5,6-pentahydroxyhexyl)amino)-2-oxo-N-phenyl-1,2-dihydroquinoline-3-carboxamide (MEG-LAQ) in the pharmaceutical composition is no more than 1.00% relative to the amount of laquinimod sodium as measured by HPLC.

In an embodiment of the pharmaceutical composition, an amount of water in the pharmaceutical composition is no more than 1.50% relative to the amount of laquinimod sodium as measured by K.F. coulometric titration.

In an embodiment of the pharmaceutical composition, an amount of water in the pharmaceutical composition is no more than 0.80% relative to the amount of laquinimod sodium as measured by K.F. coulometric titration.

In an embodiment of the pharmaceutical composition, an amount of sodium from 5.8% to 6.4% relative to the amount by weight of laquinimod sodium.

In an embodiment of the pharmaceutical composition, an amount of ethanol in the pharmaceutical composition is no more than 5000 ppm relative to the amount by weight of laquinimod sodium.

In an embodiment of the pharmaceutical composition, an amount of n-heptane in the pharmaceutical composition is no more than 5000 ppm relative to the amount by weight of laquinimod sodium;

In an embodiment of the pharmaceutical composition, an amount of n-octane in the pharmaceutical composition is no more than 2000 ppm relative to the amount by weight of laquinimod sodium.

In an embodiment of the pharmaceutical composition, an amount of methanol in the pharmaceutical composition is no more than 380 ppm relative to the amount by weight of laquinimod sodium.

In an embodiment of the pharmaceutical composition, an amount of acetone in the pharmaceutical composition is no more than 880 ppm relative to the amount by weight of laquinimod sodium.

In an embodiment of the pharmaceutical composition, an amount of dioxane in the pharmaceutical composition is no more than 380 ppm relative to the amount by weight of laquinimod sodium.

In an embodiment of the pharmaceutical composition, an amount of dimethyl formamide in the pharmaceutical composition is no more than 880 ppm relative to the amount by weight of laquinimod sodium.

The subject invention provides a method of treating a subject afflicted with a form of multiple sclerosis, lupus nephritis, lupus arthritis, rheumatoid arthritis, a BDNF-related disorder, Crohn's disease, a GABA-related disorder, a cannabinoid receptor type 1 (CB1) mediated disorder, or an ocular inflammatory disorder comprising administering to the subject the mixture of the subject invention or the pharmaceutical composition of the subject invention so as to thereby treat the subject.

The subject invention provides a method for alleviating a symptom of multiple sclerosis, lupus nephritis, lupus arthritis, rheumatoid arthritis, a BDNF-related disorder, Crohn's disease, a GABA-related disorder, a cannabinoid receptor type 1 (CB1) mediated disorder, or an ocular inflammatory disorder in a subject afflicted with a form of multiple sclerosis comprising administering to the subject the mixture of any one of the subject invention or the pharmaceutical composition of the subject invention thereby alleviating the symptom of multiple sclerosis in the subject.

In one embodiment, the mixture or the pharmaceutical composition for use in the treatment of, or alleviation of symptoms of, a form of multiple sclerosis, lupus nephritis, lupus arthritis, rheumatoid arthritis, a ROOF-related disorder, Crohn's disease, a GABA-related disorder, a cannabinoid receptor type 1 (CB1) mediated disorder, or an ocular inflammatory disorder.

The subject invention provides a use of the mixture or the pharmaceutical composition for the manufacture of a medicament for treating, or alleviating a symptom of, a form of multiple sclerosis, a GABA-related disorder, a cannabinoid receptor type 1 (CB1) mediated disorder, lupus nephritis, lupus arthritis, rheumatoid arthritis, a BDNF-related disorder, Crohn's disease, or an ocular inflammatory disorder.

The subject invention provides a process of recrystallization of laquinimod sodium comprising:
a) dissolving an amount of laquinimod sodium in water to form an aqueous solution;
b) concentrating the aqueous solution to form a concentrated solution comprising approximately 1.7-1.8 mL of water per gram of laquinimod sodium;
c) adding acetone to the concentrated solution of step b); and
d) isolating recrystallized laquinimod sodium.

In an embodiment of the process, the amount of laquinimod sodium in step a) is 2.5 kg or greater.

In an embodiment of the process, step a) is performed with 10-12 mL of water per gram of laquinimod sodium.

In an embodiment of the process, step a) is performed with approximately 11 mL of water per gram of laquinimod sodium.

In an embodiment of the process, step a) is performed by heating the aqueous solution to a temperature of 58-75° C.

In an embodiment of the process, step a) is performed by heating the aqueous solution to a temperature of 60-73° C.

In an embodiment of the process, crystallization occurs after step a) and before step c).

In an embodiment of the process, crystallization is induced by rapid stirring during or after the concentrating step b).

In an embodiment of the process, crystallization is induced by addition of a seed crystal during or after the concentrating step b).

In an embodiment of the process, crystallization occurs without addition of a seed crystal.

In an embodiment of the process, step b) is performed under conditions appropriate to induce crystallization at the concentration of 1.7-1.8 mL of water per gram of laquinimod sodium.

In an embodiment of the process, step b) is performed at 28-45° C.

In an embodiment of the process, step b) is performed at 30-40° C.

In an embodiment of the process, step c) is performed with the concentrated solution at 40-55° C.

In an embodiment of the process, step c) is performed with the concentrated solution at 45-50° C.

In an embodiment of the process, step c) is performed with 6-12 mL of acetone per gram of laquinimod sodium.

In an embodiment of the process, step c) is performed with approximately 10 mL of acetone per gram of laquinimod sodium.

In an embodiment of the process, step c) is performed over a period of 1-4 hours.

In an embodiment of the process, step c) is performed over a period of 1.2-2.5 hours.

In an embodiment of the process, step c) is followed by cooling the solution to a temperature no less than −14° C. and no more than 6° C.

In an embodiment of the process, step c) is followed by cooling the solution to a temperature no less than −4° C. and no more than 4° C.

In an embodiment of the process, the solution is cooled over a period of 3-5 hours.

In an embodiment of the process, the solution is cooled over a period of 3.5-4.5 hours.

In an embodiment of the process, step d) further comprises washing the recrystallized laquinimod sodium with 1-4 mL of acetone per gram of crude laquinimod sodium used in step a).

In an embodiment of the process, step d) further comprises washing the recrystallized laquinimod sodium with approximately 3 mL of acetone per gram of crude laquinimod sodium used in step a).

In an embodiment of the process, step d) further comprises drying the recrystallized laquinimod sodium for no less than one hour at 30-40° C. under a vacuum of no more than 50 mmHg.

In an embodiment of the process, the isolated recrystallized laquinimod sodium in step d) is a mixture of crystalline laquinimod sodium particles having a particle size distribution such that (i) 90% or more of the total amount by volume of the laquinimod sodium particles have a size of 40 microns or less, (ii) 50% or more of the total amount by volume of the laquinimod sodium particles have a size of 15 microns or less, and (iii) 10% or more of the total amount by volume of the laquinimod sodium particles have a size of less than 5 microns or less.

The subject invention provides a mixture of crystalline laquinimod sodium particles prepared by the process of the subject invention.

In an embodiment of the mixture of crystalline laquinimod sodium particles prepared by the process of the subject invention, (i) 90% or more of the total amount by volume of the laquinimod sodium particles have a size of 40 microns or less, (ii) 50% or more of the total amount by volume of the laquinimod sodium particles have a size of 15 microns or less, and (iii) 10% or more of the total amount by volume of the laquinimod sodium particles have a size of 5 microns or less.

In an embodiment of the mixture,
a) the mixture has a bulk density of 0.2 g/mL to 0.4 g/mL;
b) the mixture has a tapped density of 0.40 g/mL to 0.7 g/mL;
c) an amount of aluminium in the mixture is less than 5 ppm relative to the amount by weight of laquinimod sodium;
d) an amount of calcium in the mixture is less than 60 ppm relative to the amount by weight of laquinimod sodium;
e) an amount of copper in the mixture is less than 1 ppm relative to the amount by weight of laquinimod sodium;
f) an amount of iron in the mixture is less than 4 ppm relative to the amount by weight of laquinimod sodium;
g) an amount of zinc in the mixture is less than 7 ppm relative to the amount by weight of laquinimod sodium;
h) an amount of heavy metal in the mixture is no more than 0.002% relative to the amount by weight of laquinimod sodium;
i) a total amount of polar impurities in the mixture is no more than 1.004 relative to the amount of laquinimod sodium as measured by HPLC;
j) an amount of 5-chloro-4-hydroxy-1-methyl-2-oxo-1,2-dihydroquinoline (MCQ) in the mixture is no more than 0.15% relative to the amount of laquinimod sodium as measured by HPLC;
k) an amount of 5-chloro-4-hydroxy-1-methyl-2-oxo-1,2-dihydroquinoline-3-carboxylic acid (MCQCA) in the mixture is no more than 0.15% relative to the amount of laquinimod sodium as measured by HPLC;
l) an amount of methyl 5-chloro-4-hydroxy-1-methyl-2-oxo-1,2-dihydroquinoline-3-carboxylate (MCQME) in the mixture is no more than 0.12% relative to the amount of laquinimod sodium as measured by HPLC;
m) an amount of ethyl 5-chloro-4-hydroxy-1-methyl-2-oxo-1,2-dihydroquinoline-3-carboxylate (MCQEE) in the mixture is no more than 0.10% relative to the amount of laquinimod sodium as measured by HPLC;
n) a total amount of non-polar impurities in the mixture no more than 0.50% relative to the amount of laquinimod sodium as measured by HPLC;
o) an amount of N-ethyl aniline in the mixture is no more than 0.10% relative to the amount of laquinimod sodium as measured by HPLC;
p) an amount of laquinimod acid in the mixture is no more than 1.00% relative to the amount of laquinimod sodium as measured by HPLC;
q) an amount of dimethyl malonate in the mixture is no more than 0.10% relative to the amount of laquinimod sodium as measured by HPLC;
r) an amount of diethyl malonate in the mixture is no more than 0.10% relative to the amount of laquinimod sodium as measured by HPLC;
s) an amount of dimethyl sulfate in the mixture is no more than 1 ppm relative to the amount by weight of laquinimod sodium;
t) an amount of water in the mixture is no more than 1.5% by weight relative to the amount of laquinimod sodium as measured by K.F. coulometric titration;
u) the mixture comprises an amount of sodium from 5.8% to 6.4% relative to the amount by weight of laquinimod sodium;
v) an amount of ethanol in the mixture is no more than 5000 ppm relative to the amount by weight of laquinimod sodium;
w) an amount of n-heptane in the mixture is no more than 5000 ppm relative to the amount by weight of laquinimod sodium;
x) an amount of n-heptane in the mixture is no more than 2000 ppm n-octane relative to the amount by weight of laquinimod sodium;
y) an amount of methanol in the mixture is no more than 3000 ppm relative to the amount by weight of laquinimod sodium;
z) an amount of acetone in the mixture is no more than 5000 ppm relative to the amount by weight of laquinimod sodium;
aa) an amount of dioxane in the mixture is no more than 380 ppm relative to the amount by weight of laquinimod sodium; or
bb) an amount of dimethyl formamide in the mixture is no more than 880 ppm relative to the amount by weight of laquinimod sodium.

In an embodiment of the mixture,
a) the mixture has a bulk density of 0.2 g/mL to 0.4 g/mL;
b) the mixture has a tapped density of 0.40 g/mL to 0.7 g/mL;
c) an amount of aluminium in the mixture is less than 5 ppm relative to the amount by weight of laquinimod sodium;
d) an amount of calcium in the mixture is less than 60 ppm relative to the amount by weight of laquinimod sodium;
e) an amount of copper in the mixture is less than 1 ppm relative to the amount by weight of laquinimod sodium;

f) an amount of iron in the mixture is less than 4 ppm relative to the amount by weight of laquinimod sodium;

g) an amount of zinc in the mixture is less than 7 ppm relative to the amount by weight of laquinimod sodium;

h) an amount of heavy metal in the mixture is no more than 0.002% relative to the amount by weight of laquinimod sodium;

i) a total amount of polar impurities in the mixture is no more than 1.00% relative to the amount of laquinimod sodium as measured by HPLC;

j) an amount of 5-chloro-4-hydroxy-1-methyl-2-oxo-1,2-dihydroquinoline (MCQ) in the mixture is no more than 0.15% relative to the amount of laquinimod sodium as measured by HPLC;

k) an amount of 5-chloro-4-hydroxy-1-methyl-2-oxo-1,2-dihydroquinoline-3-carboxylic acid (MCQCA) in the mixture is no more than 0.15% relative to the amount of laquinimod sodium as measured by HPLC;

l) an amount of methyl 5-chloro-4-hydroxy-1-methyl-2-oxo-1,2-dihydroquinoline-3-carboxylate (MCQEE) in the mixture is no more than 0.12% relative to the amount of laquinimod sodium as measured by HPLC;

m) an amount of ethyl 5-chloro-4-hydroxy-1-methyl-2-oxo-1,2-dihydroquinoline-3-carboxylate (MCQEE) in the mixture is no more than 0.10% relative to the amount of laquinimod sodium as measured by HPLC;

n) a total amount of non-polar impurities in the mixture is no more than 0.50% relative to the amount of laquinimod sodium as measured by HPLC;

o) an amount of N-ethyl aniline in the mixture is no more than 0.10% relative to the amount of laquinimod sodium as measured by HPLC;

p) an amount of laquinimod acid in the mixture is no more than 1.00% relative to the amount of laquinimod sodium as measured by HPLC;

q) an amount of dimethyl malonate in the mixture is no more than 0.10% relative to the amount of laquinimod sodium as measured by HPLC;

r) an amount of diethyl malonate in the mixture is no more than 0.10% relative to the amount of laquinimod sodium as measured by HPLC;

s) an amount of dimethyl sulfate in the mixture is no more than 1 ppm relative to the amount by weight of laquinimod sodium;

t) an amount of water in the mixture is no more than 1.5% by weight relative to the amount of laquinimod sodium as measured by K.F. coulometric titration;

u) the mixture comprises an amount of sodium from 5.8% to 6.4% relative to the amount by weight of laquinimod sodium;

v) an amount of ethanol in the mixture is no more than 5000 ppm relative to the amount by weight of laquinimod sodium;

w) an amount of n-heptane in the mixture is no more than 5000 ppm relative to the amount by weight of laquinimod sodium;

x) an amount of n-heptane in the mixture is no more than 2000 ppm n-octane relative to the amount by weight of laquinimod sodium;

y) an amount of methanol in the mixture is no more than 3000 ppm relative to the amount by weight of laquinimod sodium;

z) an amount of acetone in the mixture is no more than 5000 ppm relative to the amount by weight of laquinimod sodium;

aa) an amount of dioxane in the mixture is no more than 380 ppm relative to the amount by weight of laquinimod sodium; and bb) an amount of dimethyl formamide in the mixture is no more than 980 ppm relative to the amount by weight of laquinimod sodium.

The subject invention provides a pharmaceutical composition comprising the mixture of crystalline laquinimod sodium particles prepared by the process of the subject invention, and a pharmaceutically acceptable carrier.

In an embodiment of the pharmaceutical composition, a) a total amount of 5-chloro-4-hydroxy-1-methyl-2-oxo-1,2-dihydroquinoline (MCQ) and 5-chloro-4-hydroxy-1-methyl-2-oxo-1,2-dihydroquinoline-3-carboxylic acid (MCQCA) in the pharmaceutical composition is no more than 0.50% relative to the amount of laquinimod sodium as measured by HPLC;

b) a total amount of polar impurities in the pharmaceutical composition is no more than 2.00% relative to the amount of laquinimod sodium as measured by HPLC;

c) an amount of N-ethyl aniline in the pharmaceutical composition is no more than 0.50% relative to the amount of laquinimod sodium as measured by HPLC;

d) a total amount of non-polar impurities in the pharmaceutical composition is no more than 1.00% relative to the amount of laquinimod sodium as measured by HPLC;

e) an amount of water in the pharmaceutical composition is no more than 0.80% relative to the amount of laquinimod sodium as measured by K.F. coulometric titration;

f) the pharmaceutical composition comprises an amount of sodium from 5.8% to 6.4% relative to the amount by weight of laquinimod sodium;

g) an amount of ethanol in the pharmaceutical composition is no more than 5000 ppm relative to the amount by weight of laquinimod sodium;

h) an amount of n-heptane in the pharmaceutical composition is no more than 5000 ppm relative to the amount by weight of laquinimod sodium;

i) an amount of n-octane in the pharmaceutical composition is no more than 2000 ppm relative to the amount by weight of laquinimod sodium;

j) an amount of methanol in the pharmaceutical composition is no more than 380 ppm relative to the amount by weight of laquinimod sodium;

k) an amount of acetone in the pharmaceutical composition is no more than 880 ppm relative to the amount by weight of laquinimod sodium;

l) an amount of dioxane in the pharmaceutical composition is no more than 380 ppm relative to the amount by weight of laquinimod sodium; or m) an amount of dimethyl formamide in the pharmaceutical composition is no more than 860 ppm relative to the amount by weight of laquinimod sodium.

In an embodiment of the pharmaceutical composition, a) a total amount of 5-chloro-4-hydroxy-1-methyl-2-oxo-1,2-dihydroquinoline (MCQ) and 5-chloro-4-hydroxy-1-methyl-2-oxo-1,2-dihydroquinoline-3-carboxylic acid (MCQCA) in the pharmaceutical composition is no more than 0.50% relative to the amount of laquinimod sodium as measured by HPLC;

b) a total amount of polar impurities in the pharmaceutical composition is no more than 2.00% relative to the amount of laquinimod sodium as measured by HPLC;

c) an amount of N-ethyl aniline in the pharmaceutical composition is no more than 0.50% relative to the amount of laquinimod sodium as measured by HPLC;

d) a total amount of non-polar impurities in the pharmaceutical composition is no more than 1.00% relative to the amount of laquinimod sodium as measured by HPLC;
e) an amount of water in the pharmaceutical composition is no more than 0.80% relative to the amount of laquinimod sodium as measured by K.F. coulometric titration;
f) the pharmaceutical composition comprises an amount of sodium from 5.6% to 6.4% relative to the amount by weight of laquinimod sodium;
g) an amount of ethanol in the pharmaceutical composition is no more than 5000 ppm relative to the amount by weight of laquinimod sodium;
h) an amount of n-heptane in the pharmaceutical composition is no more than 5000 ppm relative to the amount by weight of laquinimod sodium;
i) an amount of n-octane in the pharmaceutical composition is no more than 2000 ppm relative to the amount by weight of laquinimod sodium;
j) an amount of methanol in the pharmaceutical composition is no more than 380 ppm relative to the amount by weight of laquinimod sodium;
k) an amount of acetone in the pharmaceutical composition is no more than 880 ppm relative to the amount by weight of laquinimod sodium;
l) en amount of dioxane in the pharmaceutical composition is no more than 380 ppm relative to the amount by weight of laquinimod sodium; and
m) an amount of dimethyl formamide in the pharmaceutical composition is no more than 880 ppm relative to the amount by weight of laquinimod sodium.

The subject invention provides a mixture of crystalline laquinimod sodium particles, wherein (i) 90% or more of the total amount by volume of the laquinimod sodium particles have a size of 40 microns or less or (ii) 50% or more of the total amount by volume of the laquinimod sodium particles have a size of 15 microns or less, and wherein
a) an amount of aluminium in the mixture is less than 5 ppm relative to the amount by weight of laquinimod sodium;
b) an amount of calcium in the mixture is less than 60 ppm relative to the amount by weight of laquinimod sodium;
c) an amount of copper in the mixture is less than 1 ppm relative to the amount by weight of laquinimod sodium;
d) an amount of iron in the mixture is less than 4 ppm relative to the amount by weight of laquinimod sodium; or
e) an amount of zinc in the mixture is less than 7 ppm relative to the amount by weight of laquinimod sodium.

The subject invention provides a pharmaceutical composition comprising the mixture of the subject invention and a pharmaceutically acceptable carrier.

In an embodiment of the mixture, 90% or more of the total amount by volume of the laquinimod sodium particles have a size of 1 micron or greater, 2 microns or greater, 3 microns or greater or 4 microns or greater.

In an embodiment of the mixture, 90% of the total amount by volume of the laquinimod sodium particles have a size of greater than 1 micron, greater than 2 microns, greater than 3 microns, greater than 4 microns or greater than 5 microns.

In a further embodiment of the mixture, the mixture has a tapped density of 0.4 g/mL to 0.7 g/mL, 0.44 g/mL to 0.7 g/mL, 0.45 g/mL to 0.7 g/mL, 0.46 g/mL to 0.7 g/mL or 0.5 g/mL to 0.7 g/mL.

In a further embodiment of the mixture, the mixture has a bulk density of 0.2 g/mL to 0.4 g/mL, 0.2 g/mL to 0.33 g/mL, 0.2 g/mL to 0.31 g/mL.

In a further embodiment of the pharmaceutical composition, the pharmaceutical composition comprises mannitol.

In a further embodiment of the pharmaceutical composition, the pharmaceutical composition comprises meglumine.

In a further embodiment of the pharmaceutical composition, the pharmaceutical composition comprises sodium stearyl fumarate.

In a further embodiment of the pharmaceutical composition, not less than 70% of the labeled amount of laquinimod is dissolved in 30 minutes.

In a further embodiment of the pharmaceutical composition, capsules of the pharmaceutical composition contain 90-110% of the labeled amount of laquinimod.

In a further embodiment of the pharmaceutical composition, capsules of the pharmaceutical composition contain 95-105% of the labeled amount of laquinimod.

In a further embodiment of the pharmaceutical composition, capsules of the pharmaceutical composition contain 98.0-102.0% of the labeled amount of laquinimod.

In a further embodiment of the pharmaceutical composition, the pharmaceutical composition has content uniformity conforming to the U.S. Pharmacopeia.

In a further embodiment of the pharmaceutical composition, the pharmaceutical composition has content uniformity conforming to European Pharmacopeia.

Each embodiment disclosed herein is contemplated as being applicable to each of the other disclosed embodiments. Thus, all combinations of the various elements described herein are within the scope of the invention. For example, any embodiment for an element of a mixture a contemplated as being applicable to a pharmaceutical composition. As another rexample, an embodiment to a tapped density of 0.46 g/mL to 0.7 g/mL is contemplated as being applicable to a mixture having an amount of aluminium in the mixture less than 5 ppm relative to the amount by weight of laquinimod sodium.

COMPARISON TO THE PRIOR ART

Applicants have unexpectedly achieved a mixture of crystalline laquinimod sodium that is improved over the laquinimod sodium of the prior art.

The prior art U.S. Pat. No. 7,884,208 teaches a process of recrystallization of laquinimod sodium which produces and a mixture of crystalline laquinimod sodium having larger crystals, lowered impurity levels and some improved crystalline characteristics.

Specifically, U.S. Pat. No. 7,884,208 achieves a mixture of crystalline laquinimod sodium having all four of the following aspects: (i) a mixture wherein 10% or more of the total amount by volume of the laquinimod sodium particles has a size of greater than 40 microns and wherein 50% or more of the total amount by volume of the laquinimod sodium particles has a size of greater than 15 microns, (ii) high density (tapped and bulk), (iii) low heavy metal content, and (iv) low polar impurity content.

However, the recrystallization process of U.S. Pat. No. 7,884,208 (Examples 13-17, Tables 1-4) does not produce a mixture of recrystallized laquinimod sodium particles wherein 90% or more of the total amount by volume of the laquinimod sodium have a size of 40 microns or less, or 50% or more of the total amount by volume of the laquinimod sodium has a size of 15 microns or less.

Likewise, the recrystallization process of U.S. Pat. No. 7,884,208 does not produce a mixture of recrystallized laquinimod sodium particles wherein 90% or more of the total amount by volume of the laquinimod sodium have a size of less than 40 microns, wherein 50% or more of the total amount by volume of the laquinimod sodium has a size of Less than 15 microns, and wherein 10% or more of the total amount by volume of the laquinimod sodium has a size of less than 5 microns.

Example 14 of U.S. Pat. No. 7,884,208 produced a mixture of recrystallized laquinimod sodium particles wherein 10% or more of the total amount by volume of the laquinimod sodium have a size of less than 5 microns. However, this Example also shows reduced quality of crystalline characteristics, specifically Tapped Density. The mixture produced by Example 14 has an acceptable D(0.1) value but an undesired Tapped Density.

Conversely, Example 13 of U.S. Pat. No. 7,884,208 produced a mixture having high Tapped Density, but did not produce crystals wherein 90% or more of the total amount by volume of the laquinimod sodium particles have a size of 40 microns or less or 50% or more of the total amount by volume of the laquinimod sodium particles have a size of 15 microns or less.

Importantly, U.S. Pat. No. 7,884,208 is unable to achieve the advantages of recrystallization, i.e., better density and impurity profiles, while also producing laquinimod sodium crystals wherein 90% or more of the total amount by volume of the laquinimod sodium particles have a size of 40 microns cc less, or 50% or more of the total amount by volume of the laquinimod sodium particles have a size of 15 microns or less.

U.S. Pat. No. 7,884,208, by say of Example 1 (batches A, B and C) and Tables 1-3, also teaches that the process disclosed in U.S. Pat. No. 6,077,851 results in a mixture of crystalline laquinimod sodium having all four of the following aspects: (i) 90% or more of the total amount by volume of the laquinimod sodium particles have a size of 40 microns or less, or 50% or more of the total amount by volume of the laquinimod sodium particles have a size of 15 microns or less, (ii) poor density (tapped and bulk), (iii) high heavy metal content, and (iv) high polar impurity content. Importantly, although U.S. Pat. No. 6,077,851 achieves a mixture wherein 90% or more of the total amount by volume of the laquinimod sodium particles have a size of 40 microns or less or, 50% or more of the total amount by volume of the laquinimod sodium particles have a size of 15 microns or less, but it does not achieve crystals having acceptable density or low levels of impurities.

The prior art contains no teaching of a process for preparing laquinimod sodium wherein 90% or more of the total amount by volume of the laquinimod sodium particles have a size of 40 microns or less, or 50% or more of the total amount by volume of the laquinimod sodium particles have a size of 15 microns or less, and having desirable density and purity profiles.

The present invention achieves a mixture of recrystallized laquinimod sodium crystals wherein 90% or more of the total amount by volume of the laquinimod sodium particles have a size of 40 microns or less or (ii) 50% or more of the total amount by volume of the laquinimod sodium particles have a size of 15 microns or less, and having desirable density and purity profiles, specifically, (i) high density (tapped or bulk), (ii) low heavy metal content, or (iii) low polar impurity content.

The laquinimod sodium of the subject invention is achieved by an improved recrystallization process.

Improved Recrystallization Process

The laquinimod sodium manufactured by the recrystallization processes of the present invention has improved purity and density profiles over the laquinimod sodium disclosed in U.S. Pat. No. 6,077,851 and improved crystalline characteristics, especially smaller particles, over U.S. Pat. No. 7,884,208.

The modified recrystallization process of the present invention unexpectedly results in different recrystallization conditions than achieved by the process disclosed in U.S. Pat. No. 7,884,208 and, thusly, results in different products. Specifically, concentrating the aqueous solution to 1.7-1.8 unexpectedly results in crystalline laquinimod sodium particles having reduced levels of impurities, improved crystalline characteristics, and wherein 90% or more of the total amount by volume of the laquinimod sodium particles have a size of 40 microns or less, 50% or more of the total amount by volume of the laquinimod sodium particles have a size of 15 microns or less, and 10% or more of the total amount by volume of the laquinimod sodium particles have a size of 5 microns or less.

Without being limited to any one particular theory, an important factor affecting crystallization is initial concentration of crystallizing solution. Careful control of concentration of the solution can facilitate initiation of spontaneous crystallization prior to the end of the concentration step. The process of the present invention can initiate spontaneous crystallization prior to addition of acetone.

Concentrating the aqueous solution to form a concentrated solution comprising approximately 1.7-1.8 mL of water per gram of laquinimod sodium is an important aspect of the present invention.

Improved Mixture of Crystalline Laquinimod Sodium

U.S. Pat. No. 7,884,208 teaches advantages associated with large particles. Specifically, U.S. Pat. No. 7,884,208 teaches that larger particles of laquinimod sodium are more "processable" when making pharmaceutical compositions and that smaller particles are often associated with dust-like properties which may interfere with processing, and sometimes associated with flowability problems which may interfere with manufacturing. Further, U.S. Pat. No. 7,884,208 teaches that chemical stability has been shown to be decreased by the increase in surface area that results from smaller particle size. (Felmeister, A. Chpt 88, *Remington's Pharmaceutical Sciences*, $15^{th}$ Edition, Mack Publishing Company, Easton, Pa. (1975).

However, the subject invention has unexpectedly achieved an improved mixture of laquinimod sodium wherein (i) 90% or more of the total amount by volume of the laquinimod sodium particles have a size of 40 microns or less, (ii) 50% or more of the total amount by volume of the laquinimod sodium particles have a size of 15 microns or less, and (iii) 108 or more of the total amount by volume of the laquinimod sodium particles have a size of 5 microns or less.

Laqinimod has been graded as a highly potent API, demanding special caution and avoiding material contact with workers and environment. Laquinimod has been graded as having the highest potency rate, corresponding to a recommended acceptable daily intake (ADI) during operations and manufacturing of less than 0.01 mg/day or <1 $\mu g/m^3$ as an 8-hour TWA. High potency compounds are associated with controls, whether engineering, administrative or procedure-related, that afford the desired level of worker protection. For example, high potency compounds may require no human intervention or manual operations. (Bruce D. Naumann, Control Banding In The Pharmaceutical Industry, http://www.aioh.org.au/downloads/documents/ControlBandingBNaumann.pdf)

Importantly, although the mixture of the subject invention may be milled or unmilled, the present invention is achieved without the need of a milling operation.

The mixture of laquinimod sodium of the present invention overcomes the potential problems associated with mixtures having large particles. With respect to processing and manufacturing, the small size of the laquinimod sodium particles of the present invention may obviate the need for milling and comminution steps. U.S. Pat. No. 7,884,208 reflected the understanding in the art that there are problems associated with small particles in pharmaceutical compositions, but the laquinimod sodium of the present invention has no problems associated with stability, processing or manufacturing.

Comminution introduces its own set of problems to a drug substance beyond the disadvantages of introducing an additional drug processing step. For example, milling can introduce impurities, new polymorphs, amorphous sections in the crystalline structure of the API, other changes to particle morphology, differences in agglomeration, increased solubility, changes in moisture levels, and changes in compressability (Hausner, "The Role of Particle Size in the Development of Generic Products" 2003). As a result, comminution may affect the efficacy and safety of a drug substance. Some of the disadvantages of comminution are illustrated by the side effects resulting from microcrystalline Nitrofurantoin compared to macrocrystalline Nitrofurantoin. (Brumfitt, W. and J. M. T. Hamilton-Miller, *J. Antimicrobial Chemotherapy* 42:363:371 (1998)).

Accordingly, it is advantageous to produce a drug substance which does not contain large particles to avoid the inefficiencies of additional process steps such as milling or sieving. The laquinimod sodium of the present invention provides a mixture of laquinimod sodium particles having small particle sizes which avoids safety problems and additional problems related to milling.

Another concern during formulation processes is maintaining uniformity of content of the drug product. in the case of laquinimod, the unit dose of laquinimod is quite low relative to the total weight of the drug product, e.g., tablet or capsule. A typical formulation, for example, may comprise only a small amount of laquinimod, e.g., 0.3, 0.6 or 1.2 mg, in a capsule with total weight of over 200 mg. As such, small fluctuation in the amount of laquinimod due to problems of flowability, segregation, uniformity, or poor homogenous distribution could result in a large percent deviation from the desired amount, e.g., 0.3, 0.6 or 1.2 mg. The mixture of laquinimod sodium of the present invention provides high uniformity of content and minimal fluctuations in the amount of laquinimod in the capsules.

TABLE 1

Uniformity of Laquinimod Bland (UoB) and Uniformity of the content of filled capsules (UoC)

| Batch | Batch type | UoB AVG | UoB RSD | UoC | UoC AV |
|---|---|---|---|---|---|
| 1 | C | 99.5 | 1.67 | 99.3 | 4.5 |
| 2 | C | 100.6 | 0.61 | 98.7 | 2.7 |
| 3 | C | 102.6 | 1.10 | 99.9 | 2.2 |
| 4 | C | 97.3 | 0.90 | 99.4 | 4.7 |
| 5 | E | 101.3 | 1.02 | 100.6 | 2.4 |
| 6 | E | 101.3 | 1.02 | 100.8 | 3.6 |
| 7 | C | 97.4 | 0.85 | 96.4 | 5.9 |
| 8 | C | 101.6 | 1.08 | 98.6 | 2.8 |
| 9 | C | 98.5 | 0.71 | 94.2 | 8.6 |
| 10 (0.3 mg) | C | 101.2 | 0.66 | 96.9 | 8.7 |
| 11 | C | 101.2 | 0.66 | 94.6 | 7.1 |
| 12 | C | 97.1 | 1.35 | 96.8 | 5 |
| 13 | P | 95.3 | 0.88 | 98.6 | 3.5 |
| 14 | P | 98.6 | 0.91 | 101.4 | 5.2 |
| 15 | P | 97.1 | 0.59 | 96.6 | 5.7 |
| 16 | P | 98.8 | 0.58 | 98.4 | 5.3 |
| 17 | P | 98.2 | 0.54 | 98.5 | 4.3 |
| 18 | P | 97.2 | 0.96 | 100.7 | 2.4 |

TABLE 1-continued

Uniformity of Laquinimod Bland (UoB) and Uniformity of the content of filled capsules (UoC)

| Batch | Batch type | UoB AVG | UoB RSD | UoC | UoC AV |
|---|---|---|---|---|---|
| 19 | P | 102.2 | 1.20 | 100.2 | 4.6 |
| 20 | P | 102.9 | 1.82 | 98.4 | 3.3 |
| 21 | P | 103.6 | 1.01 | 99.7 | 4.4 |
| 22 | C | 97.9 | 0.5 | 98.5 | 1.4 |
| 23 | C | 98.7 | 0.5 | 99.2 | 1.6 |
| 24A | E | 95.3 | 0.7 | 94.2 | 12.1 |
| 24B | E | | | | |
| 25 | E | 97.1 | 1.2 | 98 | |
| 26A (0.6 mg) | E | 99.8 | 1.8 | 97.4 | 2.2 |
| 26B (0.6 mg) | E | 99.8 | 1.8 | 97.4 | 2.2 |

UoB: Uniformity of Blend, RSD is the parameter to describe the uniformity before filling into capsules
UoC: Uniformity of the content of the filled capsule, AV is the acceptance value which is related to RSD to uniformity.

Uniformity of the shape of laquinimod particles is also an important concern during formulation as a lack of uniformity of shape can cause variation in density of drug substance and cause problems during drug product formation, e.g., capsule or tablet formation. Crystalline laquinimod sodium particles are rod-shaped particles. It is known that milling operations may result in changes to particle shape.

Decreased particle size known to result in faster dissolution profiles. The rate of dissolution of small particles is usually faster than that of large particles because a greater surface area of the drug substance is in contact with the liquid medium. When formulating a drug with a low dissolution rate, it is desirable to decrease particle size in order to increase dissolution and thus facilitate rapid gastrointestinal or oral absorption.

In such cases where drug substances have no recognized problems associated with dissolution rate, particle size reduction may be inadvisable and even deleterious. Increasing surface area can increase degradation rates of the drug substance. As discussed, for example, in U.S. Pat. Nos. 8,178,127 and 7,989,473, laquinimod sodium is susceptible to degradation.

Unexpectedly, in spite of known disadvantages associated with small particle sizes, it was found that an improved drug substance and drug product resulted from a mixture of crystalline laquinimod sodium particles wherein (i) 90% or more of the total amount by volume of the laquinimod sodium particles have a size of 40 microns or less, (ii) 50% or more of the total amount by volume of the laquinimod sodium particles have a size of 15 microns or less, and (ill) 10% or more of the total amount by volume of the laquinimod sodium particles have a size of 5 microns or less.

Accordingly, an advantage of the recrystallization process of the present invention is that the resulting mixture of crystalline laquinimod sodium has particles having small particle sizes, which is associated with high uniformity and homogeneity with respect to distribution of the API into capsules, tablets and other drug products. Laquinimod sodium crystals having small particle sizes can obviate or reduce the need for additional milling steps. The small particle sizes of the laquinimod sodium of the present invention are achieved without sacrificing desirable purity or density profiles and without the need for prior milling operations.

Another advantage of the present invention is that laquinimod sodium crystals have a higher density than the laquinimod sodium crystals produced by the slurry-to-slurry process of U.S. Pat. No. 6,077,651. Low tapped density is anathema to certain prized qualities in a drug substance or drug product such as compressibility, the ability of a powder to decrease in volume under pressure, and compactability, the ability of a powder to be compressed into a tablet of certain strength or hardness. Crystals with low tapped density are also known to have poor flowability, which results in a lack of uniformity of content in finished dosage forms, especially in tablets. (Rudnic et al. Chpt. 45, *Remington's Pharmaceutical Sciences,* 20th Edition, Lippincott Williams & Wilkins, Baltimore, Md. (2000)) Uniformity of content is especially important for pharmaceutical compositions comprising a potent drug substance, e.g., Laquinimod sodium.

Compared to the slurry-to-slurry process of U.S. Pat. No. 6,077,851, the present invention also shows low aggregation of the particles and, additionally, provides particles with acceptable density and lower levels of impurities. As shown in FIGS. 5-8, the crude laquinimod resulting from the process described in U.S. Pat. No. 6,077,851 has a high rate of aggregates (FIGS. 5 and 6), compared to a low rate of aggregates of the present invention (FIGS. 7 and 8).

Another advantage of the present invention is that the process of the present invention is environmentally friendly without sacrificing desirable crystalline characteristics. Specifically, by use of water as the primary solvent, the present invention achieves both environmental friendliness and improved crystalline characteristics, specifically with respect to particle size distribution over U.S. Pat. No. 7,884,208.

TERMS

As used herein, and unless stated otherwise, each of the following terms shall have the definition set forth below.

As used herein, "laquinimod" means laquinimod acid or a pharmaceutically acceptable salt thereof, including laquinimod sodium.

As used herein, "laquinimod acid" is N-ethyl-N-phenyl-1, 2,-dihydro-4-hydroxy-5-chloro-1-methyl-2-oxoquinoline-3-carboxamide, and its Chemical Registry number is 248281-89-7. "Laquinimod sodium" is the sodium salt of laquinimod acid.

As used herein, D(0.1) is the particle sire, in microns, below which 10% by volume distribution of the population is found.

As used herein, D(0.5) is the particle size, in microns, below which 50% by volume distribution of the population is found.

As used herein, D(0.9) is the particle size, in microns, below which 90% by volume distribution of the population is found.

As used herein, "crystalline characteristics" includes particle size distribution, bulk density and tapped density.

As used herein, "drug substance" refers to the active ingredient in a drug product or for use in a drug product, which provides pharmacological activity or other direct effect in the diagnosis, cure, mitigation, treatment, or prevention of disease, or to affect the structure or any function of the body of man or animals.

As used herein, "drug product" refers to the formulated or finished dosage form containing the drug substance as well as at least one pharmaceutically acceptable carrier.

As used herein, a composition that is "free" of a chemical entity means that the composition contains, if at all, an amount of the chemical entity which cannot be avoided although the chemical entity is not part of the formulation and was not affirmatively added during any part of the manufacturing process. For example, a composition which is "free" of an alkalizing agent means that the alkalizing agent, if present at all, is a minority component of the composition by weight. Preferably, when a composition is "free" of a component, the composition comprises less than 0.1 wt %, 0.05 wt %, 0.02 wt %, or 0.01 wt % of the component.

As used herein, "dissolution rate" is determined based on the amount of drug substance dissolved in 30 min. as indicated in the U.S. Pharmacopeia <711>.

As used herein, "atmospheric pressure" refers to a pressure of about 1 atm.

As used herein, "ambient temperature" refers to a temperature of about 20° C. to about 30° C.

As used herein, "about" in the context of a numerical value or range means±10% of the numerical value or range recited or claimed.

As used herein, "approximately" in the context of a numerical value or range means±5% of the numerical value or range recited or claimed.

The term "stable pharmaceutical composition" as used herein in connection with the composition according to the invention denotes a composition, which preserves the physical stability/integrity and/or chemical stability/integrity of the active pharmaceutical ingredient during storage. Furthermore, "stable pharmaceutical composition" is characterized by its level of degradation products not exceeding 5% at 40° C./75% RH after 6 months or 3% at 55° C./75% RH after two weeks, compared to their level in time zero.

As used herein, "treating" and "treatment" encompasses, e.g., inducing inhibition, regression, or stasis of a disease, disorder or condition, or ameliorating or alleviating a symptom of a disease, disorder or condition. "Ameliorating" or "alleviating" a condition or state as used herein shall mean to relieve or lessen the symptoms of that condition or state. "Inhibition" of disease progression or disease complication in a subject as used herein means preventing or reducing the disease progression and/or disease complication in the subject.

"Administering to the subject" means the giving of, dispensing of, or application of medicines, drugs, or remedies to a subject to relieve, cure, or reduce the symptoms associated with a condition, e.g., a pathological condition.

The drug substance of the present invention, e.g., laquinimod sodium, may be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier.

This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsules or tablets can be easily formulated and can be made easy to swallow or chew; other solid forms include granules, and bulk powders.

Capsules or tablets may contain suitable binders, lubricants, disintegrating agents, diluents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like.

Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like.

Lubricants used in these dosage forms include sodium oleate, sodium stearate, magnesium stearate, sodium benzoate, sodium acetate, sodium chloride, and the like.

Disintegrators include, without limitation, starch, methyl cellulose, agar, bentonite, xanthan gum, and the like.

Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Oral dosage forms optionally contain flavorants and coloring agents. Parenteral and intravenous forms may also include minerals and other materials to make them compatible with the type of injection or delivery system chosen.

The compounds used in the method of the present invention may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydrcxylpropyl-methacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

For oral administration in liquid dosage form, the oral drug components are combined with any oral, non-toxic, pharmaceutically acceptable inert carrier such as ethanol, glycerol, water, and the like. Examples of suitable dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The drug substance of the present invention, e.g., laquinimod sodium, may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

A dosage unit of the compounds used in the method of the present invention may comprise a single compound or mixtures thereof with additional antibacterial agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

A "dose" or "dosage unit" of laquinimod as measured in milligrams refers to the milligrams of laquinimod acid present in a preparation, regardless of the form of the preparation. A dosage unit may comprise a single compound or mixtures of compounds thereof. A dosage unit can be prepared for oral dosage forms, such as tablets, capsules, pills, powders, and granules. For example, the "dose" or "dosage unit" of laquinimod may be 0.3, 0.6, or 1.2 mg.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject. The carrier may be liquid or solid and is selected with the planned manner of administration in mind. "Pharmaceutically acceptable carrier" includes "fillers", which fill out the size of a tablet or capsule, making it practical to produce and convenient for the consumer to use. By increasing the bulk volume, the fillers make it possible for the final product to have the proper volume for patient handling. "Pharmaceutically acceptable carrier" also includes "lubricants", which prevent ingredients from clumping together and from sticking to the tablet punches or capsule filling machine. Lubricants also ensure that tablet formation and ejection can occur with low friction between the solid and die wall. "Pharmaceutically acceptable carrier" also includes inert carriers such as lactose, gelatin, agar, starch, sucrose, glucose, methyl cellulose, dicalcium phosphate, calcium sulfate, mannitol, sorbitol, microcrystalline cellulose and the like. Liposomes are also a pharmaceutically acceptable carrier.

It is understood that where a parameter range is provided, all integers within that range, and tenths and hundredth thereof, are also provided by the invention. For example, "0.15-0.35%" includes 0.15%, 0.16%, 0.17% etc. up to 0.35%.

The subject invention is also intended to include all isotopes of atoms occurring on the compounds disclosed herein, including impurities. Isotopes include those atoms having the same atomic number but different mass numbers. By way of general example and without limitation, isotopes of hydrogen include tritium and deuterium. Isotopes of carbon including C-13 and C-14.

A "detection limit" for an analytical method used in screening or testing for the presence of a compound in a sample is a threshold under which the compound in a sample cannot be detected by the analytical method used. For example, the detection limit of a given method for detecting 5-chloro-4-hydroxy-1-methyl-2-oxo-1,2-dihydroquinoline-3-carboxylic acid (MCQCA) is 0.03% and the detecting limit of a given method for detecting methyl 5-chloro-4-hydroxy-1-methyl-2-oxo-1,2-dihydroquinoline-3-carboxylate (MCQME), 5-chloro-4-hydroxy-1-methyl-2-oxo-1,2-dihydroquinoline (MCQ), 5-chloro-4-hydroxy-1-methyl-2-oxo-1,2-dihydroquinoline-3-carboxylate (MCQEE) and unknown impurities is 0.02%

As used herein, "density" is a measurement defined as the mass of a substance per unit volume.

As used herein, "bulk density" or "BD" refers to a density measurement of a loose, uncompacted substance, wherein the volume of the substance includes the air trapped between particles.

As used herein, "tapped density" or "TD" refers to a density measurement of a substance that has been tapped or vibrated, thus minimizing the volume of the substance by eliminating or minimizing the air trapped between particles.

As used herein, "rapid stirring" refers to stirring which splashes solvent onto the walls of the vessel.

As used herein, "blend uniformity" refers to the homogeneity of blend or granulate including laquinimod sodium particles prior to encapsulation, tableting or otherwise finalizing the drug product beyond formation of the final blend, and can represent either one sample or the average of more than one sample. Blend uniformity may be measured, for example, by taking 10 samples that represent the upper, middle and lower layer of each batch of the final blend, performing an HPLC assay to measure the amount of active ingredient in the samples, and comparing the amount of active ingredient in each sample to the labeled amount of active ingredient. The standard deviation and relative standard deviation can be determined based on the individual amounts of the tested samples expressed as percentages of the labeled amount of drug substance in each sample.

As used herein, "content uniformity" refers to the homogeneity of the laquinimod sodium. content among dosage forms, e.g., capsules or tablets, after formulation. The uniformity of dosage units by content uniformity of the pharmaceutical composition described herein meets the U.S. Pharmacopeia <905> Acceptance Value and range (as specified); $L_1=15.0$ and $L_2=25.0$. Content uniformity may be measured, for example, as indicated by the United States Pharmacopoeia which includes 1) assaying ten tablets (or other dosage form of the drug product) to ensure that the relative standard deviation (RSD) of active content is less than or equal to 6.0% and no value is outside 85-115%; and 2) assaying twenty more tablets (or other dosage form of the drug product) to ensure that the RSD for all thirty is less than or equal to 7.8%, no more than one value is outside 85-115% and no value is outside 75-125% of stated content.

As used herein, "residual solvents" include ethanol, n-heptane, n-octane, methanol, acetone, dioxane, and dimethyl formamide. Residual solvents may be determined, for example, based on the manufacturer's statements of residual solvent levels in the active ingredients/excipients and calculation as per U.S. pharmacopeia <467> Option 2, product meets the USP <467> Residual Solvents limit criteria. Testing is not necessarily required.

As used herein, "NMT" means no more than.

As used herein, "MCQME" means methyl 5-chloro-4-hydroxy-1-methyl-2-oxo-1,2-dihydroquinoline-3-carboxylate. MCQME is disclosed in U.S. Pat. No. 7,560,557. MCQME has the structure:

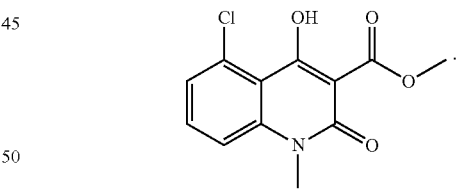

As used herein, "MCQEE" means ethyl 5-chloro-4-hydroxy-1-methyl-2-oxo-1,2-dihydroquinoline-3-carboxylate. MCQEE is disclosed in U.S. Pat. No. 7,560,557. MCQEE has the structure:

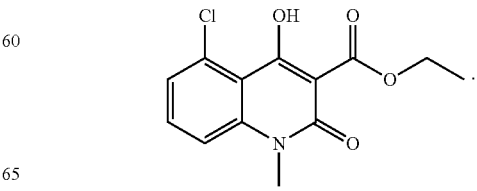

As used herein, "MCQ" means 5-chloro-4-hydroxy-1-methyl-2-oxo-1,2-dihydroquinoline. MCQ is disclosed in U.S. Pat. No. 7,560,557. MCQ has the structure:

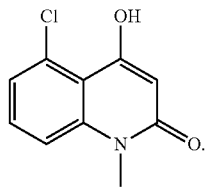

As used herein, "MCQCA" means 5-chloro-4-hydroxy-1-methyl-2-oxo-1,2-dihydroquinoline-3-carboxylic acid. MCQCA is disclosed in U.S. Pat. No. 7,560,557. MCQCA has the structure:

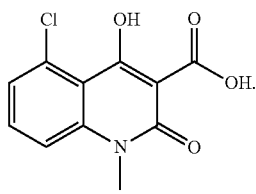 [SMILES: Cn1c(=O)c(C(=O)O)c(O)c2c(Cl)cccc21]

As used herein, "NEA" means N-ethyl aniline. NEA is disclosed in U.S. Pat. No. 7,560,557. NEA has the structure:

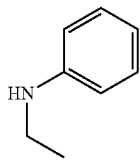

As used herein, "5-HLAQ" means N-ethyl-4,5-dihydroxy-1-methyl-2-oxo-N-phenyl-1,2,3,4-tetrahydroquinoline-3-carboxamide. 5-HLAQ is disclosed in PCT International Application No. PCT/US13/26476. 5-HLAQ has the structure:

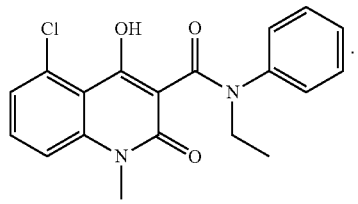 [SMILES: CCN(C(=O)c1c(O)c2c(Cl)cccc2n(C)c1=O)c1ccccc1]

As used herein, "3-HLAQ" means 5-chloro-N-ethyl-3-hydroxy-1-methy-5-2,4-dioxo-N-phenyl-1,2,3,4-tetrahydroquinoline-3-carboxamide. 3-HLAQ is disclosed in PCT International Application No. PCT/US2008/013890. 3-HLAQ has the structure:

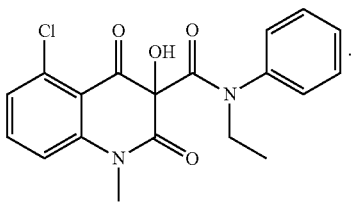 [SMILES: CCN(C(=O)C1(O)C(=O)c2c(Cl)cccc2N(C)C1=O)c1ccccc1]

As used herein, "MEG-LAQ" means N-ethyl-4-hydroxy-1-methyl-5-(methyl(2,3,4,5,6-pentahydroxyhexyl)amino)-2-oxo-N-phenyl-1,2-dihydroquinoline-3-carboxamide. MEG-LAQ is disclosed in U.S. Provisional Application No. 61/644,054. MEG-LAQ has the structure:

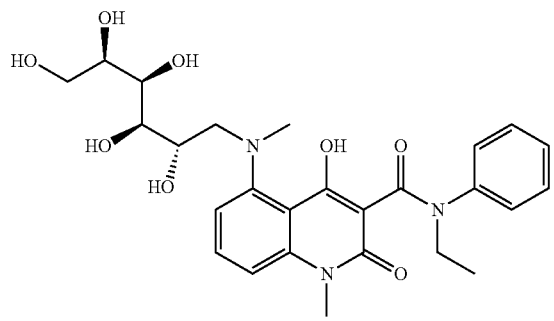

As used herein, "DELAQ" means 5-chloro-4-hydroxy-1-methyl-2-oxo-d-phenyl-1,2-dihydroquinoline-3-carboxamide. DELAQ is disclosed in PCT International Application No. PCT/US2011/043391. DELAQ has the structure:

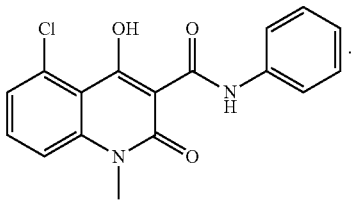 [SMILES: Cn1c(=O)c(C(=O)Nc2ccccc2)c(O)c2c(Cl)cccc21]

As used herein, "INBA" means 2-Chloro-6-(1-ethyl-N-methyl-2-oxoindoline-3-carboxamido)benzoic acid. INBA is disclosed in PCT International Application No. PCT/US2008/013890. INBA has the structure:

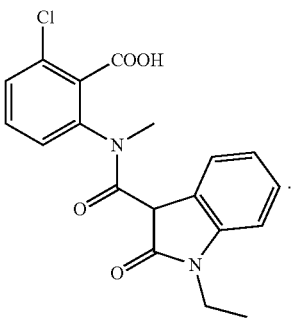 [SMILES: CCN1C(=O)C(C(=O)N(C)c2cccc(Cl)c2C(=O)O)c2ccccc21]

As used herein, "SPIRO-LAQ" means 1H,3H-spiro[5-chloro-1-methylquinoline-2,4-dione-3,3'-[1]ethylindolin-[2]-one]. SPIRO-LAQ is disclosed in PCT International Application No. PCT/US2008/013990. SPIRO-LAQ has the structure:

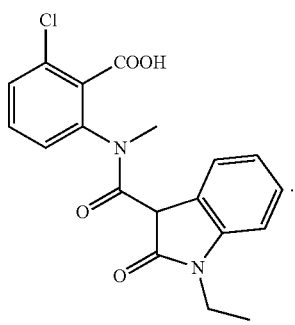 [SMILES: CCN1C(=O)C(C(=O)N(C)c2cccc(Cl)c2C(=O)O)c2ccccc21]

As used herein, "DMM" means dimethylmalonate. DMM is a synthetic reagent, and has the structure:

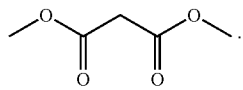

As used herein, "DMS" means Dimethyl sulfate. DMS is a synthetic reagent.

Potential impurities/degradation products are further described in Table 2.

TABLE 2

Potential Impurities/Degradation Products

| Potential Impurity/Degradation Product | Structure | Definition | Specification in Drug Substance | Specification Limits in Drug Product |
|---|---|---|---|---|
| MCQ 5-Chloro-4-hydroxy-l-methylquinolin-2(1H)-one | 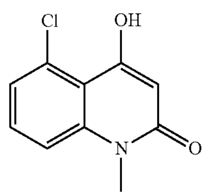 | Synthetic impurity, potential degradant | NMT 0.15% | NMT 0.5% for sum of MCQ and MCQCA |
| MCQCA 5-Chloro-4-hydroxy-1-methyl-2-oxo-1,2-dihydro-quinoline-3-carboxylic acid | 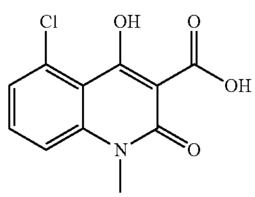 [SMILES: Cn1c(=O)c(C(=O)O)c(O)c2c(Cl)cccc21] | Synthetic impurity, potential degradant | NMT 0.15% | NMT 0.5% for sum of MCQ and MCQCA |
| MCQME Methyl 5-chloro-4-hydroxy-1-methyl-2-oxo-1,2-dihydro-quinoline-3-carboxylase | 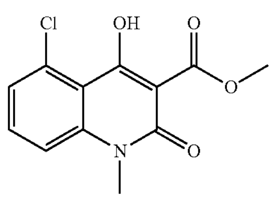 [SMILES: COC(=O)c1c(O)c2c(Cl)cccc2n(C)c1=O] | Synthetic impurity | NMT 0.15% | — |
| NEA N-Ethylaniline | 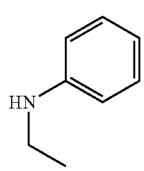 | Synthetic impurity, potential degradant | N MT 0.10% | — |
| MCQEE Ethyl 5-chloro-4-hydroxy-1-methyl-2-oxo-1,2-dihydro-quinoline-3-carboxylate | 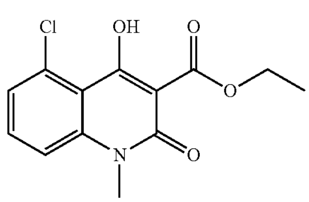 [SMILES: CCOC(=O)c1c(O)c2c(Cl)cccc2n(C)c1=O] | Synthetic impurity | NMT 0.10% | — |

TABLE 2-continued

Potential Impurities/Degradation Products

| Potential Impurity/Degradation Product | Definition | Specification in Drug Substance | Specification Limits in Drug Product |
|---|---|---|---|
| 5-HLAQ N-Ethyl-4,5-dihydroxy-1-methyl-2-oxo-N-phenyl-1,2-dihydroquinoline-3-carboxamide | Synthetic impurity, potential photo-degradant | NMT 0.10% | NMT 0.5% |
| DELAQ 5-Chloro-4-hydroxy-1-methyl-2-oxo-N-phenyl-1,2-dihydroquinoline-3-carboxamide | Synthetic impurity | NMT 0.1% | — |
| LAQ 5-Chloro-N-ethyl-4-hydroxy-1-methyl-2-oxo-N-phenyl-1,2-dihydroquinoline-3-carboxamide | Synthetic impurity, potential degradant, active moiety | NMT 1.0% | — |
| SPIRO-LAQ 1H,3H-spiro[5-chloro-1-methylquinoline-2,4-dione-3,3'-[1]ethylindolin-[2]-one] | Potential oxidation product | — | — |
| INBA 2-Chloro-6-(1-ethyl-N-methyl-2-osoindoline-3-carboxamido)benzoic acid | Potential secondary degradation product (degradation of SPIRO-LAQ) | — | — |
| 3-HLAQ 5-Chloro-N-ethyl-3-hydroxy-1-methyl-2,4-dioxo-N-phenyl-1,2,3,4-tetrahydroquinoline-3-carboxamide | Potential oxidation product | — | — |
| DMM Dimethyl malonate | Synthetic impurity (residual reagent) | NMT 0.1 % | — |

TABLE 2-continued

Potential Impurities/Degradation Products

| Potential Impurity/Degradation Product | Structure | Definition | Specification in Drug Substance | Specification Limits in Drug Product |
|---|---|---|---|---|
| DMS Dimethyl sulfate | — | Synthetic potentially genotoxic impurity (residual reagent) | NMT 1 ppm | — |
| MEG-LAQ N-ethyl-4-hydroxy-1-methyl-5-(2,3,4,5,6-pentahydroxy-hexylamino)-2-oxo-N-phenyl-1,2-dihydroquinoline-3-carboxamide | 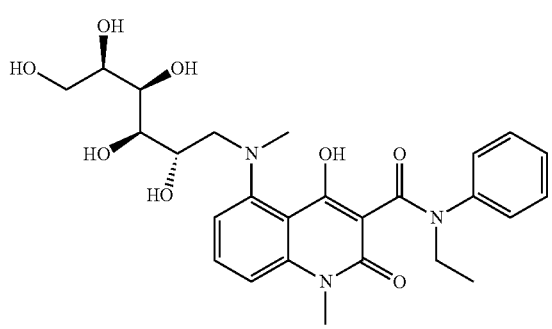 [SMILES: CCN(C(=O)c1c(O)c2c(N(C)C[C@H](O)[C@@H](O)[C@H](O)[C@H](O)CO)cccc2n(C)c1=O)c1ccccc1] | Potential DP impurity/degradation product (adduct of laquinimod sodium with one of the excipients (meglumine)) | — | NMT 1.0% |

DS = drug substance;
DP = drug product

Impurities are measured by common pharmacopeial methods unless otherwise specified.

As used herein, an "anti-solvent" is a solvent in which laquinimod sodium is slightly soluble, very slightly soluble, practically insoluble, or insoluble at room temperature (20-25° C.). The solubility terms are defined below, in accordance with the United States Pharmacopoeia XXV.

| Term | Parts of solvent required for 1 part solute |
|---|---|
| Slightly soluble | From 100 to 1000 |
| Very slightly soluble | From 1000 to 10,000 |
| Practically insoluble | 10,000 and over |
| Insoluble | 10,000 and over |

Specific examples of the techniques, pharmaceutically acceptable carriers and excipients that may be used to formulate oral dosage forms of the present invention are described, e.g., in U.S. Pat. No. 7,589,208. For example, the oral dosage form of the present invention may comprise an alkaline-reacting component, said component preferably amounting from about 1 to 20% by weight of the formulation in order to keep the pH above 8.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman at al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

The purification of impure crystalline compounds is usually attained by recrystallization from a suitable solvent or mixture of solvents. (Vogel's Textbook of Practical Organic Chemistry. $5^{th}$ edition. Longman Scientific I Technical, 1989.) The recrystallization process generally comprises the following steps: a) dissolving the impure crystalline substance in a suitable solvent near the boiling point; b) filtering the hot solution from particles of insoluble material and dust; c) allowing the hot solution to cool to cause the dissolved substance to crystallize out; and d) separating the crystals from the supernatant solution. (Id.) However, standard recrystallization techniques were accompanied by low or no yields when applied to laquinimod sodium as taught in U.S. Pat. No. 7,884,208. As shown in Examples 2-7 of U.S. Pat. No. 7,884,208, attempts to recrystallize laquinimod sodium using standard recrystallization procedures resulted in poor yields, if any. The process of U.S. Pat. No. 7,884,208 overcomes the difficulties associated with recrystallizing laquinimod sodium by use of an anti-solvent in which laquinimod sodium is practically insoluble. In addition, the process of U.S. Pat. No. 7,284,208 concentrates the laquinimod sodium aqueous solution before the addition of the anti-solvent. The process of the present invention is an improvement over the process of U.S. Pat. No. 7,884,208.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Determination of Powder Density

Bulk Density
1. Mix powder;
2. Tare a 50 rid empty cylinder on a 0.01 g sensitivity balance;
3. Transfer the powder, without compacting, to the cylinder being held at approximately a 45 degree angle to achieve an untapped apparent volume of 40 to 50 ml.
4. Bring the cylinder containing the sample to a vertical position by a sharp move in order to level the volume for reading.
5. Read the apparent volume (Va) to the nearest graduated unit;
6. Weigh the cylinder with sample (the balance gives sample weight M);
7. Calculate bulk density in g/ml according to the following equation: BD=M/Va;
B. Perform steps 1-7 again and report the average data of duplicates.

Tapped Density
1. Put the same cylinder used to calculate Bulk Density in a Quantachrome Dual Autotap instrument;
2. Perform 1250 taps;
3. Read the tapped volume (Vf) to the nearest graduated unit;
4. Calculate the tapped density in g/mL according to the following equation: TD M/Vf;
5. Perform steps 1-4 again and report the average data of duplicates.

Determination of Particle Size

The particle size distributions were measured by Malvern Laser Diffraction, using the Mastersizer S model. Laser diffraction relies on the fact that diffraction angle of light is inversely proportional to particle size. Properties of particles are measured and interpreted as measurements of a sphere (a sphere being the only shape that can be described by one unique number). In addition, laser diffraction calculates a particle size distribution based around volume terms, thus eliminating particle count from the determination of particle size. The Mastersizer S model measures particles using a single technique and a single range setting.

D(0.1) is the particle size, in microns, below which 10% by volume distribution of the population is found. D(0.5) is the particle size, in microns, below which 50% by volume distribution of the population is found. D(0.9) is the particle size, in microns, below which 90% by volume distribution of the population is found.

Determination of Heavy Metals

Metal content was measured using inductively coupled plasma atomic emission spectrometry using an inductively coupled plasma atomic emission spectrometry ("ICP-AES") system manufactured by Spectro (Kleve, Germany). Sample digestion was performed in 65% nitric acid, and the internal standard used was scandium.

Note: In the following examples the volumes of solvents used are calculated relative to starting weight of laquinimod sodium. The yields are calculated in weight percent.

Determination of Purity

Laquinimod sodium and polar impurity/degradation products were determined by isocratic reversed phase high performance liquid chromatography (RP-HPLC), using an ODS-3V column and a mobile phase comprised of a mixture of ammonium acetate buffer at pH 7.0 (80%) and acetonitrile (20%). The detection technique was ultraviolet absorption at 240 nm.

Specific HPLC Conditions:
Column & Packing: Inertsil ODS-3V, 5 μm, 4.6×250 mm, GL Sciences Inc.
Guard column: Opti-Guard C 18, 1×10 mm
Mobile phase: Acetonitrile:Buffer pH 7.0-20:80 (v/v). Mix and degas
Buffer pH 7.0 preparation: Dissolve 7.7 g Ammonium acetate in 2000 mL water and adjust to pH 7.0±0.05 with aqueous ammonia or glacial acetic acid. Filter through a 0.45 μm membrane filter.
Flow rate: 1.5 μL/min
Detection: UV at 240 nm
Injection volume: 50 μL
Diluent A: Acetonitrile/Water—50:50 (v/v)
Diluent B (and blank): Mobile Phase
Column temperature: 40° C.
Autosampler temperature: 5° C.
Run time: 40 minutes Typical HPLC Procedure:
1. Standard Solutions Preparation
1.1 Laquinimod Standard Stock Solution (Solution S)

Weigh accurately in duplicate about 15 mg of laquinimod sodium standard into a 50 mL volumetric flask. Dilute with diluents A up to ⅔ of the volume, sonicate for 2 minutes in a cold sonication bath and dilute to volume with diluents A.

Concentration of standard stock solution is about 300 μg/mL laquinimod sodium. Standard stock solution may be used for one month when stored in a refrigerator 2° C.-8° C.

1.2 Laquinimod Standard Working Solution for Assay (Solution A)

Dilute 3 mL of the Standard Stock Solution to 10 mL with diluents B (dilution factor 3.33).

Concentration of Laquinimod sodium is about 90 μg/mL.

Concentration expressed as laquinimod (acid) is about 85 μg/mL.

Standard working solution A may be used. for 7 days when stored in a refrigerator (2° C.-8° C.).

1.3 MCQCA Standard Stock Solution

Weigh accurately about 18 mg of MCQCA standard into a 100 mL volumetric flask. Dilute to volume with acetonitrile, sonicate (in a cold sonication bath) until the substance is completely dissolved—stock MCQCA solution.

Concentration of MCQCA is about 180 μg/mL.

MCQCA Stock standard solution should be freshly prepared.

1.4 Standard Solution for Determination of Impurities (Solution I)

Prepare a solution in diluents B, containing Laquinimod in a concentration of 0.2% and MCQCA—in a concentration of 0.1%, with respect to the working concentration of Laquinimod in Standard solution A. As an example, apply the following procedure.

Transfer 4.0 mL of laquinimod sodium standard solution for assay (Solution A) and 1.0 mL of MCQCA stock standard solution to a 100 mL volumetric flask and dilute to volume with the diluents B (intermediate dilution).

Place 2.5 mL of this intermediate dilution into a 50 mL volumetric flask and make up to volume with diluents B.

Total dilution factor for laquinimod standard is 1666.67, for MCQCA 2000.

Concentration of laquinimod sodium is about 0.18 μg/mL (0.2%)

Concentration of MCQCA is about 0.09 μg/mL (0.1%, QL level).

Standard solution I may be used for 24 hours when stored in a refrigerator.

2. Resolution Solutions Preparation 2.1 Mixed Solution Prepare solution containing the following potential impurities standards (markers) using the Diluent A as a solvent:

Mixed Solution:
MCQ: 5-Chloro-4-hydroxy-1-methylquinolin-2(1H)-one
MCQCA: 5-Chloro-4-hydroxy-1-methyl-2-oxo-1,2-dihydroquinoline-3-carboxylic acid
MCQMA: Methyl 5-Chloro-4-hydroxy-1-methyl-2-oxo-1,2-dihydroquinoline-3-carboxylate
5-HLAQ: N-Ethyl-4,5-dihydroxy-1-methyl-2-oxo-N-phenyl-1,2-dihydroquinoline-3-carboxamide The Mixed Solution may be prepared as follows:

Weigh about 3 mg of each impurity standard/marker into a 100 mL volumetric flask, dissolve (sonication is acceptable) and dilute to volume with the Diluent A.

Concentration of each impurity in the Mixed Solution is about 30 µg/mL. Mixed Solution may be used for up to 4 months when stored frozen at about −20° C. For this purpose, the freshly prepared Mixed Solution should be divided into aliquots, immediately frozen and stored at −20° C. After thawing, the aliquots should be mixed well and should not be refrozen.

2.2 Stock Solutions of Additional Impurities

Weigh about 3 mg of MCQEE (Ethyl 5-Chloro-4-hydroxy-1-methyl-2-oxo-1,2-dihydroquinoline-3-carboxylate) into a 100 mL volumetric flask, dissolve (sonication is acceptable) and dilute to volume with the Diluent A. This is MCQEE Stock solution.

This solution may be used for up to 4 months when stored frozen at about −20° C.

For this purpose, the freshly prepared MCQEE Stock Solution should be divided into aliquot, immediately frozen and stored at −20° C. After thawing, the aliquots should be mixed well and should not be refrozen.

Weigh about 3 mg of MEG-LAQ (Meglumine Adduct of Laquinimod) into a 100 mL volumetric flask, dissolve (sonication is acceptable) and dilute to volume with the Diluent A. This is MEG-LAQ Stock solution.

This solution may be used for one week when stored in refrigerator (2° C.-8° C.).

2.3 Resolution Solutions

Prepare two Resolution Solutions separately as follows, using the Mixed Solution.

2.3.1 Resolution Solution 1

Transfer 3 mL of laquinimod standard stock solution (solution S), 0.3 mL of the Mixed Solution and 0.3 mL of the MCQEE Stock solution to a 10 mL volumetric flask and dilute to volume with the Diluent B. This is Resolution Solution 1.

Concentration of laquinimod sodium in it is about 90 µg/mL. Concentration of each impurity—is about 0.9 µg/mL (about 1% with respect to the working concentration of laquinimod).

Resolution Solution 1 is used for resolution test (for system suitability) and for determination of retention times (RT)/ relative retention times (RRT) of five impurities: MCQ, MCQCA, MCQME, MCQEE, and 5-HLAQ.

Resolution Solution 1 may be used for 9 days if stored in a refrigerator 2° C.-8° C.).

2.3.2 Resolution Solution 2

Transfer 3 mL of laquinimod standard stock solution (solution S), 0.3 mL of the Mixed Solution and 0.3 mL of the MEG-LAQ Stock solution to a 10 mL volumetric flask and dilute to volume with the Diluent B. This is Resolution Solution 2.

Concentration of laquinimod sodium in it is about 90 µg/mL.

Concentration of each impurity—is about 0.9 µg/mL (about 1% with respect to the working concentration of laquinimod).

Resolution Solution 2 is used for determination of retention time of MEG-LAQ.

Resolution Solution 2 may be used for 9 days if stored in a refrigerator 2° C.-8° C.).

3. Sample Solution Preparation

Weigh accurately 20 capsules and completely empty their contents into a mortar. Pay attention to complete emptying of capsule contents into the mortar, using spatula when necessary. Weigh the empty capsules. Calculate the average weight of the capsule contents. Mix and grind the capsule contents in a mortar and keep the powder in a tightly closed container protected from light.

Weigh accurately, in duplicate, the amount of powder corresponding to 7 capsules, into a 50 mL volumetric flask.

Add diluents B up to ⅔ of the volume, shake for 30 minutes at 200 mot/min. Dilute to volume with Diluent B. Mix well. Filter before use through a 0.45 µm GHP ACRODISC GF filter or equivalent, discarding the first 0.5-1 mL.

Working concentration of laquinimod (acid) is about 84 ug/mL. Immediately after preparation place sample solutions into a refrigerator or in a cooled to 5° C. autosampler. The sample solutions may be used for 24 hours when kept at the temperature 2° C.-8° C.

4. Procedure

Inject the Resolution Solutions, Diluent B (Blank), Standard Solutions for assay and IDD and Sample solutions, according to standard operating procedures.

Determine the retention time (RT) and the area of the laquinimod peak in the chromatograms of Sample and Standard Solutions for identification and assay.

Determine the RT, the relative retention time (RRT) and peak areas of all known impurities and any other impurities in the chromatograms of Sample Solutions, for calculation of the content of impurities/degradation products.

Ignore early elution peaks of excipients and system peaks (See chromatogram for determination of impurities/degradation products). For example. Use integration inhibition between 0 and RRT 0.15 (about 2.5 minutes).

Adjust integration parameters to reject peaks with area less than 10% of the average response of Laquinimod peak in the injections of Standard Solution I (for determination of impurities/degradation products).

Disregard peak of MEG-LAQ in sample injections (identified following Resolution Solution 2). The content of MEG-LAQ is tested by a different method.

5. System Suitability Test 5.1 Resolution Test

Typical retention time of laquinimod peak is 15.5±2.0 minutes.

Tailing factor (USP) for laquinimod peak should be not more than 2.0.

Resolution factor for all the pairs of peaks should be not less than (NLT) 2.

RRT of the peaks of known impurities/degradation products should be as follows:
MCQME: 0.33-0.38
MCQ: 0.49-0.59

MCQEE 0.56-0.65
MCQCA: 0.71-0.85
5-HLAQ: 1.2-1.4 (Should not be more than 23 minutes)

MEG-LAQ peak is substantially broadened in comparison with neighboring peaks. Retention time of MEG-LAQ is variable, being very sensitive to slightest changes in chromatographic conditions (pH, 8 acetonitrile, Temperature, etc.) and therefore should be defined using its peak in the chromatogram of the Resolution Solution 2. Typically, its RRT is about 0.66.

5.2 System Precision Test

Evaluate laquinimod standards for assay and IDD in order to test the system precision according to the standard operating procedures.

MCQCA in Solution I is used to test the sensitivity of the system. RSD of the area of six injections of Std 1 as well as the difference between Std 1 and Std 2 should be no more than (NMT) 20%.

5.3 Blank

Injection diluents B to detect system peaks.

6. Identification by Retention Time (RT)

The RT of the main peak obtained in the sample chromatogram should correspond to that obtained for the laquinimod peak in the injection of Standard Solution.

7. Calculation and Report 7.1 Assay Calculation $$\% \text{ Assay (to Label Claim)} = \frac{Area_{Smp} \times Conc_{Std} \times 0.94 \times V_{Smp} \times AvgWt_{CapsContent}}{Area_{Std} \times W_{Smp} \times \text{Label Claim}}$$

Where 0.94 is the conversion factor of laquinimod sodium salt to laquinimod (acid).

7.2 Calculation and Evaluation of Impurities/Degradation Products 7.2.1 Calculation of Relative Retention Time (RRT)

$$RRT \text{ Impurity} = \frac{RT \text{ Impurity}}{RT \text{ Laquinimod}}$$

7.2.2 Calculation of Content of Impurities/Degradation Products $$\% \text{ Impurity} = \frac{Area_{Impurity} \times Conc_{Std} \times V_{Smp} \times AvgWt_{CapsContent} \times 0.94 \times RRF}{Area_{Std} \times W_{Smp} \times \text{Label Claim}}$$

$Area_{impurity}$ is the area of an impurity/degradation product (known or unknown) peak in the Sample Solution.

$Area_{std}$ is the laquinimod peak in chromatogram of Standard Solution I.

0.94 is the conversion factor of laquinimod sodium salt to laquinimod (acid).

RRF is the relative response factors of impurities/degradation products calculated as the following ratio: slope of Laquinimod regression line/slope of impurity regression line.

The values for relative response factors with respect to laquinimod are: MCQME: 0.74; MCQ: 0.65; MCQEE: 0.85; MCQCA: 0.62; and 5-HLAQ: 1.0.

RRF for unknown impurities/degradation products is taken as 1.0.

7.2.3 Evaluation and Report of Impurities/Degradation Products

Quantitation level (QL) MCQME, MCQ, MCQEE, 5-HLAQ, and unknown impurities is 0.05%. Detection level (DL) of MCQME, MCQ, MCQEE, 5-HLAQ and unknown impurities is 0.02%. QL of MCQCA is 0.1%. Detection level DL of MCQCA is 0.03%.

Correlate all the peaks in sample chromatogram with those in the system suitability chromatogram, with ±5% of the actual corresponding retention times. Report data as shown in Table 3.

TABLE 3

Reporting Guidelines for HPLC data

| | Result | Report |
|---|---|---|
| Specified impurities | | |
| 5-HLAQ | ≥0.05% | The calculated result |
| | <0.05% | <0.05% |
| | <0.02% (or ND) | <0.02% |
| MCQ and MCQCA sum | ≥0.01% | The calculated result |
| | <0.01% | <0.01% |
| | <0.03% (or ND) | <0.03% |
| Other impurities | | |
| MCQME, MCQEE | ≥0.05% | The calculated result |
| | <0.05% | <0.05% |
| | <0.02% (or ND) | <0.02% |
| Unknown peaks (by RRT to laquinimod) | ≥0.05% | The calculated result |
| | <0.05% | <0.05% |
| | <0.02% (or ND) | Not to be reported* |
| Total | ≥0.05% | The sum of calculated results |
| | <0.05% (or <0.02% or ND) | <0.05% |

*If no impurities were detected, report: any other <0.2%.

TABLE 4

Example System Suitability Results 1

| | Name | RT | RT Ratio | Area | USP Resolution | USP Trailing | Int Type |
|---|---|---|---|---|---|---|---|
| 1 | MCQME | 5.460 | 0.36 | 35801 | | 1.07 | BB |
| 2 | MCQ | 8.260 | 0.54 | 60687 | 8.2 | 1.16 | BV |
| 3 | MCQEE | 9.249 | 0.6 | 24029 | 2.6 | 1.05 | VB |
| 4 | MCQCA | 12.031 | 0.78 | 18609 | 5.7 | 1.34 | BB |
| 5 | Laquinimod | 15.332 | | 12332469 | 5.2 | 1.84 | BB |
| 6 | 5-HLAQ | 20.451 | 1.33 | 89463 | 7.3 | 1.04 | BB |

Example 1

Modified Recrystallization of Laquinimod Sodium—Pilot Production, 100 Fold Scale-Up, (Pilot Scale Batches A and B)

Re-crystallization of Laquinimod Na on pilot scale is performed in two glass-lined reactors (Reactor A, 30 liter volume and Reactor B 60 liter). Solid product is filtered and dried in Hastelloy C agitated filter-deer with 20 micron mesh.

Batch size is 2.5 kg of starting de Laquinimod Na.

Batch of crude Laquinimod Na (2.5 kg) is introduced to Reactor A with 10 volumes of process water. The batch is heated to 60-73° C. at stirring until complete dissolution of solid.

The hot solution in Reactor A is transferred to Reactor B through 0.2 μm filtration system. Reactor A and filters washed with 1.2 volumes of process water and the wash is transferred to the Reactor B.

Vacuum is built-up and the solution in the Reactor B is evaporated at 0<45 mmHg and jacket temperature T<65° C. until volume of the residue reaches 5.4 liters (2.16 volumes). Then atmospheric pressure is built-up and jacket temperature 40-50° C. is adjusted.

The batch is stirred for not less than 10 minutes and then seeded with Laquinimod Na crystals to initiate crystallization.

The hatch is stirred at 45° C. for additional 90 minutes and 7.9 volumes of acetone are added to the reactor in 1.5-2.5 hrs.

Reactor temperature during the addition maintained between 40 and 50° C.

Resulting slurry is cooled to 0±4° C. during 3.5-4.5 hrs and stirred at this temperature for 10-15 hrs. Then the slurry is transferred to filter-dryer and solid is filtered under pressure of nitrogen.

The cake is washed twice (2·2 kg) with acetone, purged with nitrogen and then dried under vacuum (P<50 mmHg) and elevated temperature (T=40° C.) at agitation.

Dry product is discharged, sampled for analysis and packed.

Discussion of Example 1

The pilot scale process of recrystallization of laquinimod sodium was based on Example 15 of U.S. Pat. No. 7,884,208. The starting material was crude laquinimod sodium having low particle size (d(0.1)=1-2μ, d(0.5)=5-11μ; d(0.9)=20-35μ) and appears as aggregated solid. Example 15 of U.S. Pat. No. 7,884,208 involves 25.0 g of laquinimod sodium, (laboratory scale) prepared according to the method disclosed in U.S. Pat. No. 6,875,869. In Example 15, the 25.0 g of laquinimod sodium is dissolved in an aqueous solution of laquinimod sodium and then evaporated under vacuum at stirring to a concentrated solution having a volume ratio of 2.14 v/w, the resulting residue is seeded to induce crystallization then treated with an anti-solvent (acetone).

The modified pilot scale process was performed with 2.5 kg of laquinimod sodium which is a 100-fold scale up from Example 15. In addition, the modified pilot scale process had significant differences from the laboratory scale process of Example 15 of U.S. Pat. No. 7,884,208. Specifically, evaporation on the laboratory scale was performed in a round-bottom flask in a rotary evaporator without stirring, while evaporation on the pilot scale was performed in a reactor with stirring. On the pilot scale, the evaporation residue is stirred aggressively, liquid splashes on the reactor walls, solid depositions form, and crystallization was spontaneous. On the laboratory scale, a metastable solution could be concentrated to a volume ratio of 2.1-2.2 v/w at which point crystallization did not take place and nucleation was controlled by seeding. On the pilot scale, conditions and concentration were such that spontaneous crystallization took place, i.e., crystallization was induced without seeding.

Surprisingly, the pilot batches did not result in laquinimod sodium particles having a particle size distribution expected based on Example 15 of U.S. Pat. No. 7,884,208. Instead, applicants unexpected found that the pilot batches resulted in a mixture of recrystallized laquinimod sodium particles wherein (i) 90% or more of the total amount by volume of the laquinimod sodium particles have a size of less than 40 microns, (ii) 50% or more of the total amount by volume of the laquinimod sodium particles have a size of less than 15 microns, and (iii) 10% or more of the total amount by volume of the laquinimod sodium particles have a size of less than 5 microns. A comparison of particle size distributions resulting from the two different processes is shown in Table 5.

TABLE 5

| PSD by Malvern | Laboratory Scale 25 g batch | Modified Pilot Scale 2.5 kg batch | |
|---|---|---|---|
| | Example 15 from U.S. Pat. No. 7,884,208 | Pilot Scale Batch A | Pilot Scale Batch B |
| d(0.1) um | 6.1 | 3.3 | 4.1 |
| d(0.5) um | 21.2 | 12.9 | 13.5 |
| D(0.9) um | 51.8 | 33.8 | 33.9 |
| Appearance | White free-flowing powder | White free-flowing powder | White free-flowing powder |

The process of U.S. Pat. No. 7,884,208 and the process of Example 1, above, each produce different products and are not equivalent processes. Applicants' pilot scale version of the process of U.S. Pat. No. 7,584,208 resulted in substantially different conditions from the prior art and resulted in a substantially different product having smaller particle sizes as shown in Table 5.

Since laquinimod Na is a potent drug substance, small particle size is advantageous for this API. Formation of non-aggregated laquinimod sodium crystals with reduced particle size could provide better uniformity of drug product and avoid milling or de-lumping operations. The starting material, crude laquinimod sodium, appears as aggregated solid. The re-crystallized product is free flowing powder. Powders with smaller particles have a stronger trend to aggregate. Crude laquinimod sodium prepared by slurry-to-slurry recrystallization (i.e., the process of U.S. Pat. No. 6,077,851) produces particles having a low particle size and are highly aggregated. The modified process produces particles having a low particle size and are free flowing.

The aim was scalable crystallization procedure giving smaller crystal size, PSD and low aggregation on laboratory, pilot and commercial scale. The desirable PSD profile was the following: d(0.1)<5 μm, d(0.5)<15 μm and d(0.9)<40 μm. The method is based on spontaneous crystallization initiated in aqueous phase prior to acetone addition. The important factor affecting crystallization is initial concentration of crystallizing solution. In the new crystallization procedure, reduced water volume ratio in the end of evaporation from 2.14 v/w to 1.7-1.8 v/w. Higher concentration of the solution ensures initiation of spontaneous crystallization in the end of evaporation operation and provides higher supersaturation level and lower crystal size.

Example 2

Recrystallization of Laquinimod Sodium—Laboratory Scale (Laboratory Scale Batch A)

All operations of Laquinimod Na re-crystallization step including evaporation were performed on laboratory scale in transparent agitated glass reactors equipped with stirrer, thermometers and circulating bath for heating and cooling.

25 g crude Na Laquinimod and 275 ml deionized water introduced into 250 ml stirred jacketed glass reactor. The mixture is stirred and heated to 70° C., after complete dissolution of the solid the solution is filtered through paper filter. Resulting clear filtrate introduced to 250 ml jacketed glass reactor equipped with circulating bath, stirrer, thermometer and vacuum distillation system.

Vacuum is applied and water is distilled at stirring, pressure during the evaporation is 38-40 mbar and jacket temperature is 55° C.

After distillation of ca. ⅔ volume spontaneous crystallization on the reactor wall above liquid level is observed.

The distillation is continued until the residue volume reaches 45 ml then atmospheric pressure is build up and the batch is stirred at 50° C. for one hour. On this step intensive crystallization takes place.

200 ml acetone is added to the resulting slurry in one hour and the batch is stirred for one additional hour at 50° C.

The batch is cooled to 0-5° C. during one hour and filtered on Büchner filter. The solid cake is washed with 75 ml of acetone.

Collected wet product (28.0 g) is dried in oven under vacuum at 50° C. to constant weight.
Dry product—23.8 g
Crystallization yield—95.2%
Analysis:
Microscopic Observation—Rod-Shape Particles
Particle Size Distribution by Malvern:
D(0.1)=2.3 μm
D(0.5)=10.8 μm
D(0.9)=32.7 μm Example 3

Recrystallization of Laquinimod Laboratory—Scale (Laboratory Scale Batch B)

All operations of Laquinimod Na re-crystallization step including evaporation were performed on laboratory scale in transparent agitated glass reactors equipped with stirrer, thermometers and circulating bath for heating and cooling.

25 g Na Laquinimod crude and 275 ml deionized water introduced into 250 ml stirred jacketed glass reactor. The mixture is stirred and heated to 70° C., after complete dissolution of the solid the solution is filtered through paper filter. Resulting clear filtrate introduced to 250 ml jacketed glass reactor equipped with circulating bath, stirrer, thermometer and vacuum distillation system. Vacuum is applied and water is distilled at stirring, pressure during the evaporation is 38-40 mbar and jacket temperature is 55° C. During the distillation spontaneous crystallization on the reactor wall is observed when the residue volume reached ca. 120 ml. The distillation is continued until the residue volume reaches 45 ml then atmospheric pressure is build up and the batch is stirred at 50° C. for one hour. On this step intensive crystallization takes place.

200 ml acetone is added to the resulting slurry in one hour and the batch is stirred for one additional hour at 50° C.

The batch is cooled to 0-5° C. during one hour, stirred at this temperature for one additional hour and filtered on Büchner filter. The solid cake is washed with 75 ml of acetone.

Collected wet product (27.5 g) is dried in oven under vacuum at 50° C. to constant weight.
Dry product—23.65 g
Crystallization yield—94.6%
Analysis:
Microscopic Observation—Rod-Shape Particles
Particle Size Distribution by Malvern:
D(0.1)=2.6 μm
D(0.5)=12.4 μm
D(0.9)=34.3 μm

TABLE 6

Laboratory scale Laquinimod Na crystallization results

| Laboratory Scale Batch No. | | Laboratory Scale Batch A | Laboratory Scale Batch B |
|---|---|---|---|
| Starting material, crude Laquinimod Na, g | | 25 g | 25 g |
| Dry product, g | | 23.8 g | 23.65 g |
| Crystallization yield, % | | 95.2% | 94.6% |
| PSD | D(0.1)μm | 2.3 | 2.6 |
| | D(0.5)μm | 10.8 | 12.4 |
| | D(0.9)μm | 32.7 | 34.3 |

Discussion of Examples 2 and 3

The results of Examples 2 and 3 are summarized in Table 6. Table 6 shows that the process reliably produces a mixture of laquinimod sodium crystals a mixture of recrystallized laquinimod sodium particles wherein (i) 90% or more of the total amount by volume of the laquinimod sodium particles have a size of less than 40 microns, 50% or more of the total amount by volume of the laquinimod sodium particles have a size of less than 15 microns, and (iii) 10% or more of the total amount by volume of the laquinimod sodium particles have a size of less than 5 microns.

Example 4

Recrystallization of Laquinimod Sodium—Production Scale (Production Scale Batches C, D and E)

Re-crystallization of Laquinimiod Na. on the production scale is performed in two 250 liter glass-lined reactors (Reactor I and Reactor II). Solid product is filtered and dried in Hastelloy C-22 agitated filter-dryer with 20 micron mesh.

Batch size is 6.5-7.5 kg of dry A

Batch of crude Laquinimod Na is introduced to Reactor I with 11 volumes of process water. The batch is heated to 60-73° C. at stirring until complete dissolution of solid.

The hot solution n Reactor I is circulated through 0.2 μm filtration system at heating and stirring during 15-20 minutes. After the circulation completion filtered solution is transferred to Reactor II through 0.2 μm filter. Reactor I and filters washed with 1.75 volumes of process water and the wash is transferred to the Reactor II.

Vacuum is build-up and the solution in the Reactor II is evaporated at P<45 mmHg and jacket temperature T<65° C. until volume of the residue reaches 14-16 liter (ca. 1.7-1.8 v/w water/weight crude laquinimod Na starting material). On this step spontaneous crystallization is initiated on the reactor walls. Then atmospheric pressure is build-up and jacket temperature 40-50° C. is adjusted. The batch is stirred for not less than 10 minutes.

The batch is stirred at 45° C. for additional 90 minutes and 7.9 volumes of acetone are added to the reactor in 1.5-2.5 hrs. Reactor temperature during the addition maintained between 40 and 50° C.

Resulting slurry cooled to 0±4° C. during 2-5 hrs and stirred at this temperature for 10-15 hrs. Then the slurry is transferred to filter-dryer and solid is filtered under pressure of nitrogen.

The cake is washed twice (2×10 liter) with acetone, purged with nitrogen and then dried under vacuum (P<50 mmHg) and elevated temperature (T-35±5° C.) at agitation.

Dry product is discharged, sampled for analysis and packed.

Data for typical production GMP batches is summarized in Table 7. The PSD values presented in Table 7 are in a good accordance to the results of laboratory scale experiments presented in Examples 2 and 3.

TABLE 7

Production scale Laquinimod Na crystallization results

| Production Scale Batch No. | Batch C | Batch D | Batch E |
|---|---|---|---|
| Starting material, crude Laquinimod Na, kg | 8.50 | 8.55 | 9.45 |
| Dry product, kg | 7.40 | 7.00 | 6.80 |
| Crystallization yield, % | 87 | 82 | 72 |
| Product Apperance | White free-flowing powder | White free-flowing powder | White free-flowing powder |

TABLE 7-continued

Production scale Laquinimod Na crystallization results

| Production Scale Batch No. | | Batch C | Batch D | Batch E |
|---|---|---|---|---|
| Bulk Density, g/ml | | 0.308 | 0.288 | 0.245 |
| Tapped Density, g/ml | | 0.609 | 0.609 | 0.460 |
| PSD | D(0.1)μm | 4.1 | 4.1 | 2.5 |
| | D(0.5)μm | 14.0 | 14.7 | 9.5 |
| | D(0.9)μm | 32.0 | 33.6 | 21.0 |

Batch C and D also have reduced levels of impurities (Table 8) and good bulk and tapped density (Table 7).

Analysis of powder density of laquinimod sodium produced on the production scale (22 crystallization batches) shows that the bulk density varies in range between 0.237 and 0.364 g/ml. Tapped density is with 0.432 and 0.609 g/ml.

The results of analyzing Batches C and D are shown in Tables 9 and 9.

TABLE 8

Analytical Results

| Test | | Specifications | Batch C | Batch D |
|---|---|---|---|---|
| Assay (by HPLC) | | 98.0-102.0% | 99.3% | 99.9% |
| Related Polar Substances (by HPLC) | MCQ | NMT 0.15% | LT 0.02% | LT 0.02% |
| | MCQCA | NMT 0.15% | LT 0.03% | LT 0.03% |
| | MCQEE | NHT 0.10% | LT 0.02% | LT 0.02% |
| | MCQME | NMT 0.12% | LT 0.02% | LT 0.02% |
| | 5-HLAQ | NMT 0.10% | LT 0.02% | LT 0.02% |
| | Any other impurities | NMT 0.10% | LT 0.02% | LT 0.02% |
| | Total impurities | NMT 1.00% | LT 0.05% | LT 0.05% |
| Related Non-Polar Substances (by HPLC) | N-Ethyl aniline | NMT 0.10% | LT 0.02% | LT 0.02% |
| | Any other impurities | NMT 0.10% | LT 0.02% | LT 0.02% |
| | Total impurities | NMT 0.50% | LT 0.02% | LT 0.02% |
| Des-ethyl laquinimod (DELAQ) content (by HPLC) | | NMT 0.10% | LT 0.1% | LT 0.1% |
| LAQ content by HPLC) | | NMT 1.00% | LT 0.2% | LT 0.2% |
| Dimethylmalonate content (by HPLC) | | NMT 0.10% | LT 0.05% | LT 0.05% |
| Dimethyl sulfate content (by LC-MS) | | NMT 1 ppm | LT 1 ppm | LT 1 ppm |
| Water (by K. F coulometric) | | NMT 1.5% (w/w | 0.3% (w/w) | 0.2% (w/w) |
| Heavy metals (by IPC-AES) | | NMT 0.002% ppm | LT 20 ppm | LT 20 ppm |
| Sodium content | | 5.8-6.4% | 6.1% | 6.1% |
| Residual solvents | Ethanol | NMT 5000 ppm | LT 5 ppm | LT 5 ppm |
| | n-Heptane | NMT 5000 ppm | LT 10 ppm | LT 10 ppm |
| | n-octane | NMT 2000 ppm | LT 10 ppm | LT 10 ppm |
| | Methanol | NMT 3000 ppm | LT 30 ppm | LT 30 ppm |
| | Acetone | NMT 5000 ppm | LT 250 ppm | LT 250 ppm |
| | Dioxane | NMT 380 ppm | LT 10 ppm | LT 10 ppm |
| | DMF | NMT 880 ppm | LT 40 ppm | LT 40 ppm |
| Microbiological tests | Total viable aerobic count | NMT 1000 CFU/g | LT 10 CFU/g | LT 10 CFU/g |
| | Fungi/yeasts and moulds | NMT 100 CFU/g | LT 10 CFU/g | LT 10 CFU/g |
| | *Escherica Coli* | Absence of E-Coli | Absence | Absence |

TABLE 9

Metal impurities in PPM of Laquinimod Sodium

| Impurity | Example 1, (Batch D) of U.S. Pat. No. 7,884,208 | Example 17 of U.S. Pat. No. 7,884,208 | Example 4 New Batch C | Example 4 New Batch D |
|---|---|---|---|---|
| Al | 14.0 | 5.6 | 1.63 | 1.13 |
| Ca | 165 | 65 | 6.3 | 22 |
| Cr | 2.6 | <0.5 | 0.55 | <0.26 |
| Cu | 2.8 | 1.3 | 0.325 | <0.26 |
| Fe | 31.5 | 5.8 | 3.44 | 3.55 |
| Ni | 5.5 | <0.5 | 0.79 | 0.61 |
| S | 466 | <1 | 6.7 | 3.9 |
| Zn | 20.5 | 7.5 | <1 | 3.15 |

TABLE 10

Purification of Laquinimod Sodium from MCQME

| | Starting material, Crude | Re-crystallized product |
|---|---|---|
| Batch No. | Crude | C |
| Appearance | Aggregated white solid | Free-flowing white powder |
| MCQME by HPLC, % | 0.10 | N.D.* |

*N.D.—Not Detected (<0.02%)

Microscopic photographs of typical batches of Crude and re-crystallized Laquinimod Na at different magnification are presented on FIGS. 1-4.

Discussion of Example 4

The modified crystallization procedure demonstrates good reproducibility of particle size distribution on the production scale. Reduction of the evaporation residue volume to a ratio of 1.7-1.8 v/w and initiation of spontaneous crystallization provided desirable crystal size. Improved crystallization procedure demonstrates reduction in crystal size to a level of d(0.9)<40 μm and good reproducibility of Particle Size Distribution on the production scale.

The product with reduced crystal size has no trend to aggregation and does not need milling or de-lumping for homogenization. The product with similar PSD prepared by slurry-to-slurry procedure is aggregated and thus problematic in formulation.

The modified crystallization procedure also results in laquinimod sodium having desirable density and purity profiles.

The improved crystallization procedure also provides effective purification from organic impurities, e.g., MCQME.

The data shown in Table 10 demonstrates complete removal of MCQME impurity by re-crystallization of commercial scale batch of Laquinimod sodium. Since this intermediate has genotoxic potential it should be purified to undetectable level. The crystallization process provides also purification of all other known organic impurities to the level below the limit of detection.

Figure 5:
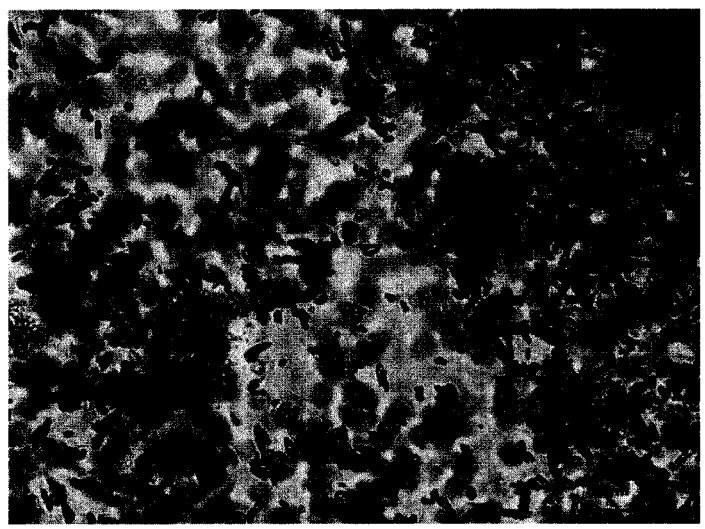
FIG. 5: Microscopic photograph of typical batch of crude Laquinimod Sodium at a first magnification level.
Figure 6:
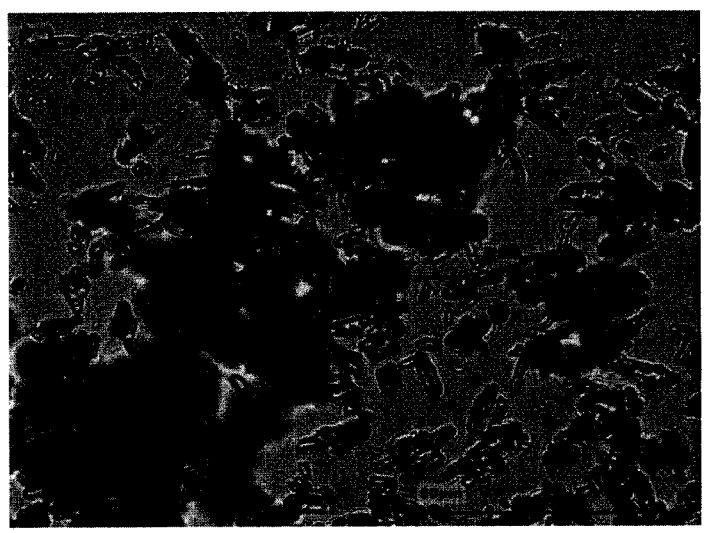
FIG. 6: Microscopic photograph of typical batch of crude Laquinimod Sodium at a second magnification level.
Figure 7:
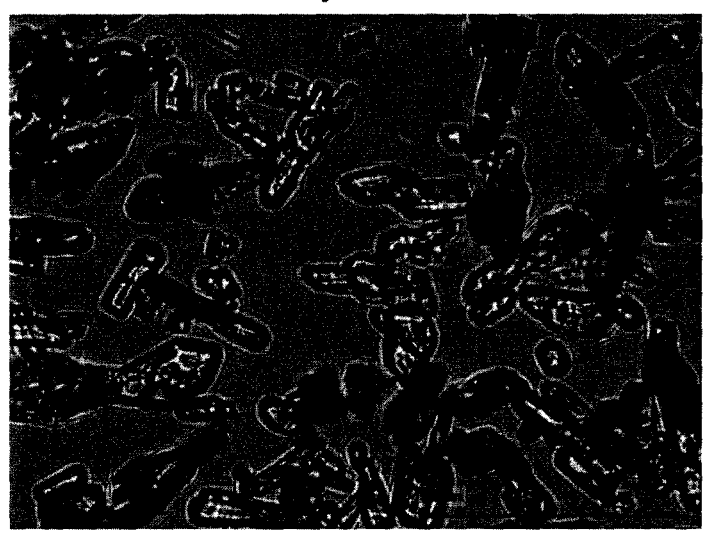
FIG. 7: Microscopic photograph of Batch C at a first magnification level.
Figure 8:
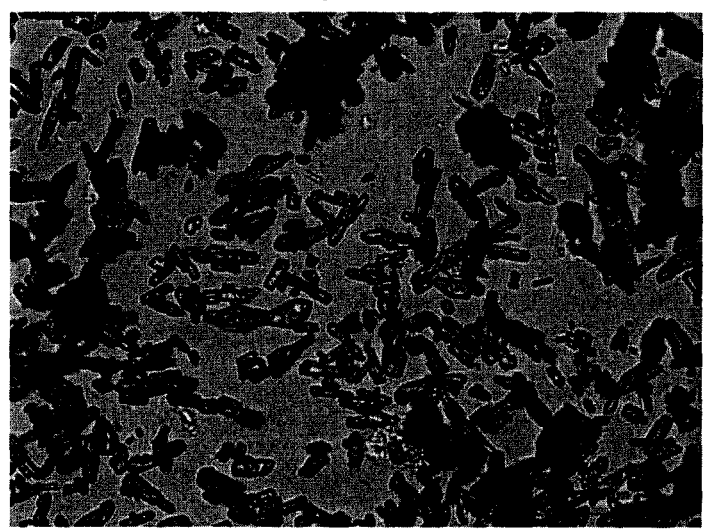
FIG. 8. Microscopic photograph of Batch C at a second magnification level.

Microscopic photographs of typical batches of crude and re-crystallized Laquinimod sodium at different magnification are presented on FIGS. 5-8 and show rod-shape morphology of the both products. At the same time the Crude presented on FIGS. 5 and 6 are much more aggregated than the re-crystallized "Cryst" product of FIGS. 7 and 8.

Example 5

Laquinimod Capsules of Pharmaceutical Composition of Laquinimod Sodium

Laquinimod capsules are manufactured according to the method as described in Example 2 of PCT International Application Publication No, WO 2007/146248, the entire content of which is hereby incorporated by reference. Steps of Example 2 of WO 2007/146245 are performed. Each capsule contains 0.64 mg of laquinimod sodium equivalent to 0.6 mg laquinimod.

The capsule has quantities of impurities below the following limits based on HPLC relative to the amount of laquinimod.

TABLE 11

Impurities in Laquinimod Capsules

| Impurity | Amount |
|---|---|
| Sum of MCQ and MCQCA | NMT 0.5% |
| 5-HLAQ | NMT 0.5% |
| Any Other Polar Impurity/Degradation Product | NMT 0.5% |
| Total Polar Impurities | NMT 2.0% |
| N-Ethylaniline | NMT 0.5% |
| 3-HLAQ | NMT 0.5% |
| Any Other Non-Polar Impurity/Degradation Product | NMT 0.5% |
| Total Non-polar Impurities | NMT 1.0% |
| MEG-LAQ | NMT 1.0% |

The capsules have a water content of no more than 1.5%.

The dissolution profiles, content uniformity, and residual solvents of the encapsulated pharmaceutical composition conforms to U.S. Pharmacopeia <711> (dissolution), U.S. Pharmacopeia <905> (uniformity), and U.S. Pharmacopeia <467>.

Each capsule contains 90.0-110.0% of the labeled amount.

The capsules contain a total aerobic microbial count (TAMC) of NMT $10^3$ cfu/g, a total combined yeasts/moulds count (TYMC) of NMT $10^2$ cfu/g, and an absence of Escherichia Coli in 1 g.

Discussion of Example 5

Example 5 demonstrates that, in a commercial-scale production, pharmaceutical compositions of laquinimod can be prepared with non-detectable levels or a low level of polar impurities and non-polar impurities.

REFERENCES

1. U.S. Pat. No. 6,077,851;
2. U.S. Pat. No. 6,875,869;
3. U.S. Pat. No. 7,589,208;
4. U.S. Pat. No. 7,864,208;
5. U.S. Pat. No. 7,989,473;
6. U.S. Pat. No. 8,178,127;
7. U.S. Patent App Publication No. 2006/0169581 A1;
8. PCT international Application Publication No. WO 2005/074899;
9. 21 C.F.R. 9211.166;
10. Felmeister, A. Chpt 89, Remington's Pharmaceutical Sciences, 15th Edition, Mack Publishing Company, Easton, Pa. (1975);
11. Hausner, "The Role of Particle Size in the Development of Generic Products" 2003;

12. Brumfitt, W. and J. M. T. Hamilton-Miller, *J. Antimicrobial Chemotherapy* 42:363:371 (1998);
13. Rudnic et al. Chpt. 45, *Remington's Pharmaceutical Sciences*, 20th Edition, Lippincott Williams & Wilkins, Baltimore, Md. (2000);
14. United States Pharmacopeia XXV (2000);
15. United States Pharmacopeia 34/National Formulary 29, (2011);
16. 7 Modern Pharmaceutics, Chapters 9 and 10 (Banker & Rhodes, Editors, 1979);
17. Pharmaceutical Dosage Forms: Tablets (Lieberman at al., 1981);
18. Ansel, Introduction to Pharmaceutical Dosage Forms 2nd Edition (1976);
19. Remington's Pharmaceutical Sciences, 17th ed. (Mack Publishing Company, Easton, Pa., 1995);
20. Advances in Pharmaceutical Sciences (David Ganderton, Trevor Jones, Eds., 1992);
21. Advances in Pharmaceutical Sciences Vol. 7. (David Ganderton, Trevor Jones, James McGinity, Eds., 1995);
22. Aqueous Polymeric Coatings for Pharmaceutical Dosage Forms (Drugs and the Pharmaceutical Sciences, Series 36 (James McGinity, Ed., 1989);
23. Pharmaceutical Particulate Carriers: Therapeutic Applications: Drugs and the Pharmaceutical Sciences, Vol 61 (Alain Rolland, Ed., 1993);
24. Drug Delivery to the Gastrointestinal Tract (Ellis Horwood Books in the Biological Sciences. Series in Pharmaceutical Technology; J. G. Hardy, S. S. Davis, Clive G. Wilson, Eds.) (1989);
25. Modem Pharmaceutics Drugs and the Pharmaceutical Sciences, Vol 40 (Gilbert S. Banker, Christopher T. Rhodes, Eds.) (1996); and
26. Vogel's Textbook of Practical Organic Chemistry. 5th edition. Longman Scientific & Technical, 1989.

What is claimed is:

1. A mixture of crystalline laquinimod sodium particles, wherein 1) (i) 90% or more of the total amount by volume of the laquinimod sodium particles have a size of 40 microns or less and (ii) 50% or more of the total amount by volume of the laquinimod sodium particles have a size of 15 microns or less, or 2) (i) 90% or more of the total amount by volume of the laquinimod sodium particles have a size of less than 40 microns and (ii) 50% or more of the total amount by volume of the laquinimod sodium particles have a size of less than 15 microns, and wherein:
   a) the mixture has a bulk density of 0.2 g/mL to 0.4 g/mL;
   b) the mixture has a tapped density of 0.40 g/ml, to 0.7 g/ml;
   c) an amount of heavy metal in the mixture is no more than 0.002% of heavy metal relative to the amount by weight of laquinimod sodium;
   d) an amount of 5-chloro-4-hydroxy-1-methyl-2-oxo-1,2-dihydroquinoline (MCQ) in the mixture is no more than 0.15% relative to the amount of laquinimod sodium as measured by HPLC;
   e) an amount of 5-chloro-4-hydroxy-1-methyl-2-oxo-1,2-dihydroquinoline-3-carboxylic acid (MCQCA) in the mixture is no more than 0.15% relative to the amount of laquinimod sodium as measured by HPLC; or
   f) an amount of methyl 5-chloro-4-hydroxy-1-methyl-2-oxo-1,2-dihydroquinoline-3-carboxylate (MCQME) in the mixture is no more than 0.12% relative to the amount of laquinimod sodium as measured by HPLC.

2. The mixture of claim 1, wherein 10% or more of the total amount by volume of the laquinimod particles have a size of 5 microns or less and wherein:
   a) the mixture has a tapped density of 0.40 q/mL to 0.7 g/mL; or
   b) an amount of 5-chloro-4-hydroxy-1-methyl-2-oxo-1,2-dihydroquinoline (MCQ) in the mixture is no more than 0.15% relative to the amount of laquinimod sodium as measured by HPLC.

3. The mixture of crystalline laquinimod sodium particles of claim 1, wherein (i) 90% or more of the total amount by volume of the laquinimod sodium particles have a size of less than 40 microns, (ii) 50% or more of the total amount by volume of the laquinimod sodium particles nave a size of less than 15 microns, and (iii) 10% or more of the total amount by volume of the laquinimod sodium particles have a size of less than 5 microns and wherein:
   the mixture has a bulk density of 0.2 g/mL to 0.4 g/mL;
   the mixture has a tapped density of 0.40 g/mL to 0.7 g/mL;
   an amount of heavy metal in the re is no more than 0.002% of heavy metal relative to the amount by weight of laquinimod sodium;
   d) an amount of 5-chloro-4-hydroxy-1-methyl-2-oxo-1,2-dihydroquinoline (MCQ) in the mixture is no more than 0.15% relative to the amount of laquinimod sodium as measured by HPLC;
   e) en amount of 5-chloro-4-hydroxy-1-methyl-2-oxo-1,2-dihydroquinoline-3-carboxylic acid (MCQCA) in the mixture is no more than 0.15% relative to the amount of laquinimod sodium as measured by HPLC; or
   f) an amount of methyl 5-chloro-4-hydroxy-1-methyl-2-oxo-1,2-dihydroquinoline-3-carboxylate (MCQME) in the mixture is no more than 0.12% relative to the amount of laquinimod sodium as measured by HPLC.

4. The mixture of claim 1, wherein,
   a) it is prepared in a single batch comprising 2.5 kg or more of laquinimod sodium,
   b) the size and amount by volume of laquinimod sodium particles are determined based on an unmilled sample of the mixture, or the size and amount by volume of laquinimod sodium particles are determined based on a milled sample of the mixture,
   c) an amount of aluminum in the mixture is less than 5 ppm or less than 2 ppm relative to the amount by weight of laquinimod sodium,
   d) an amount of calcium in the mixture is less than 60 ppm or less than 25 ppm relative to the amount by weight of laquinimod sodium,
   e) an amount of copper in the mixture is less than 1 ppm or less than 0.6 ppm relative to the amount by weight of laquinimod sodium,
   f) an amount of iron in the mixture is less than 4 ppm or less than 3.6 ppm relative to the amount by weight of laquinimod sodium,
   g) an amount of zinc in the mixture is less than 7 ppm or less than 4 ppm relative to the amount by weight of laquinimod sodium,
   h) an amount of heavy metal in the mixture is no more than 2 ppm relative to the amount by weight of laquinimod sodium,
   i) an amount of ethyl 5-chloro-4-hydroxy-1-methyl-2-oxo-1,2-dihydroquinoline-3-carboxylate (MCQEE) in the mixture is no more than 0.10% relative to the amount of laquinimod sodium as measured by HPLC,
   j) a total amount of non-polar impurities in the mixture no more than 0.50% relative to the amount of laquinimod sodium as measured by HPLC,
   k) an amount of N-ethyl aniline in the mixture is no more than 0.10% relative to the amount of laquinimod sodium as measured by HPLC, l) an amount of N-ethyl-4,5-dihydroxy-1-methyl-2-oxo-N-phenyl-1,2,3,4-tetrahydroquinoline-3-carboxamide (5-HLAQ) in the mixture is no more than 0.10% relative to the amount of laquinimod sodium as measured by HPLC, m) an amount of 5-chloro-4-hydroxy-1-methyl-2-oxo-N-phenyl-1,2-dihydroquinoline-3-carboxamide (DELAQ) in the mixture is no more than 0.10% relative to the amount of laquinimod sodium as measured by HPLC, n) an amount of laquinimod acid in the mixture is no more than 1.00% relative to the amount of laquinimod sodium as measured by HPLC, o) an amount of dimethyl malonate in the mixture is no more than 0.10% relative to the amount of laquinimod sodium as measured by HPLC, p) an amount of diethyl malonate in the mixture is no more than 0.10% relative to the amount of laquinimod sodium as measured by HPLC, q) or amount of dimethyl sulfate in the mixture is no more than 1 ppm relative to the amount by weight of laquinimod sodium, r) an amount of water in the mixture is no more than 1.5% by weight relative to the amount of laquinimod sodium as measured by K.F. coulemetric titration, s) an amount of sodium from 5.8% to 6.4% relative to the amount by weight of laquinimod sodium, t) an amount of ethanol in the mixture is no more than 5000 ppm relative to the amount by weight of laquinimod sodium, u) an amount of n-heptane in the mixture is no more than 5000 ppm relative to the amount by weight of laquinimod sodium, v) an amount of n-octane in the mixture is no more than 2000 ppm relative to the amount by weight of laquinimod sodium, w) an amount of methanol in the mixture is no more than 3000 ppm relative to the amount by weight of laquinimod sodium, x) an amount of acetone in the mixture is no more than 5000 ppm relative to the amount by weight of laquinimod sodium, y) an amount of dioxane in the mixture is no more than 380 ppm relative to the amount by weight of laquinimod sodium, z) an amount of dimethyl formamide in the mixture is no more than 880 ppm relative to the amount by weight of laquinimod sodium, and/or aa) a total amount of polar impurities in the mixture is no more than 1.00% relative to the amount of laquinimod sodium as measured by HPLC.

5. A pharmaceutical composition comprising the mixture of claim 1 and a pharmaceutically acceptable carrier.

6. The pharmaceutical composition of claim 5, wherein
a) a total amount of 5-chloro-4-hydroxy-1-methyl-2-oxo-1,2-dihydroquinoline (MCQ) and 5-chloro-4-hydroxy-1-methyl-2-oxo-1,2-dihydroquinoline-3-carboxylic acid (MCQCA) in the pharmaceutical composition is no more than 0.50% relative to the amount of laquinimod sodium as measured by HPLC, b) a total amount of polar impurities in the pharmaceutical composition is no more than 2.00% relative to the amount of laquinimod sodium as measured by HPLC, c) an amount of N-ethyl aniline in the pharmaceutical composition is no more than 0.50% relative to the amount of laquinimod sodium as measured by HPLC, d) an amount of 5-chloro-N-ethyl-3-hydroxy-1-methyl-5-2,4-dioxo-N-phenyl-1,2,3,4-tetrahydroquinoline-3-carboxamide (3-HLAQ) in the pharmaceutical composition is no more than 0.50 relative to the amount of laquinimod sodium as measured by HPLC, e) a total amount of non-polar impurities in the pharmaceutical composition is no more than 1.00% relative to the amount of laquinimod sodium as measured by HPLC, f) an amount of N-ethyl-4-hydroxy-1-methyl-5-(methyl(2,3,4,5,6-pentahydroxyhexyl)amino)-2-oxo-N-phenyl-1,2-dihydroquinoline-3-carboxamide (MEG-LAQ) in the pharmaceutical composition is no more than 1.00% relative to the amount of laquinimod sodium as measured by HPLC, g) an amount of water in the pharmaceutical composition is no more than 1.50% relative to the amount of laquinimod sodium, as measured by K.F. coulometric titration, h) an amount of water in the pharmaceutical composition is no more than 0.80% relative to the amount of laquinimod sodium as measured by K.F. coulometric titration, i) an amount of sodium from 5.8% to 6.4% relative to the amount by weight of laquinimod sodium, j) an amount of ethanol in the pharmaceutical composition is no more than 5000 ppm relative to the amount by weight of laquinimod sodium, k) an amount of n-heptane in the pharmaceutical composition is no more than 5000 ppm relative to the amount by weight of laquinimod sodium, l) an amount of n-octane in the pharmaceutical composition is no more than 2000 ppm relative to the amount by weight of laquinimod sodium, m) an amount of methanol in the pharmaceutical composition is no more than 3000 ppm relative to the amount by weight of laquinimod sodium, n) an amount of acetone in the pharmaceutical composition is no more than 5000 ppm relative to the amount by weight of laquinimod sodium, o) an amount of dioxane in the pharmaceutical composition is no more than 380 ppm relative to the amount by weight of laquinimod sodium, p) an amount of dimethyl formamide in the pharmaceutical composition is no more than 880 ppm relative to the amount by weight laquinimod sodium, and/or q) an amount of N-ethyl-4,5-dihydroxy-1-methyl-2-oxo-N-phenyl-1,2,3,4-tetrahydroquinoline-3-carboxamide (5-HLAQ) in the pharmaceutical composition is no more than 0.50% relative to the amount of laquinimod sodium as measured by HPLC.

7. A method of treating a subject afflicted with, or for alleviating a symptom of, a form of multiple sclerosis, lupus nephritis, lupus arthritis, rheumatoid arthritis, a BDNF-related disorder, Crohn's disease, a GABA-related disorder, a cannabinoid receptor type 1 (CH1) mediated disorder, or an ocular inflammatory disorder comprising administering to the subject the mixture of claim 1 or a pharmaceutical composition comprising the mixture and a pharmaceutically acceptable carrier, so as to thereby treat or alleviate the symptom in the subject.

8. A process of recrystallization of laquinimod sodium comprising:
a) dissolving an amount of laquinimod sodium in water to form an aqueous solution;
b) concentrating the aqueous solution to form a concentrated solution comprising approximately 1.7-1.9 mL of water per gram of laquinimod sodium;
c) adding acetone to the concentrated solution of step b); and
d) isolating recrystallized laquinimod sodium.

9. The process of claim 8, wherein
a) the amount of laquinimod sodium in step a) is 2.5 kg or greater,
b) step a) is performed with 10-12 mL or approximately 11 mL of water per gram of laquinimod sodium,
c) step a) is performed by heating the aqueous solution to a temperature of 58-75° C. or 60-73° C.,
d) crystallization occurs after step a) and before step c),
   a. wherein crystallization is induced by rapid stirring during or after the concentrating step b),
   b. wherein crystallization is induced by addition of a seed crystal during or after the concentrating step b), or
   c. wherein crystallization occurs without addition of a seed crystal,
e) step b) is performed under conditions appropriate to induce crystallization at the concentration of 1.7-1.8 mL of water per gram of laquinimod sodium,
f) step h) is performed at 28-45° C. or 30-40° C.,
g) step c) is performed with the concentrated solution at 40-55° C. or 45-50° C.,
h) step c) is performed with 6-12 mL or approximately 10 mL of acetone per gram of laquinimod sodium,
i) step c) is performed over a period of 1-4 hours or over a period of 1.2-2.5 hours,
j) step c) is followed by cooling the solution to a temperature no less than −14° C. and no more than 6° C. or optionally no less than −4° C. and no more than 4° C.,
k) the solution cooled over a period of 3-5 hours or over a period of 3.5-4.5 hours,
l) step d) further comprises washing the recrystallized laquinimod sodium with 1-4 mL or approximately 3 mL of acetone per gram of crude laquinimod sodium used in step a), and/or
m) step d) further comprises drying the recrystallized laquinimod sodium for no less than one hour at 30-40° C. under a vacuum of no more than 50 mmHg.

10. The process of claim 8, wherein the isolated recrystallized laquinimod sodium in step d) is a mixture of crystalline laquinimod sodium particles having a particle size distribution such that (i) 90% or more of the total amount by volume of the laquinimod sodium particles have a size of 40 microns or less, (ii) 50% or more of the total amount by volume of the laquinimod sodium particles have a size of 15 microns or less, and (iii) 10% or more of the total amount by volume of the laquinimod sodium particles have a size of use than 5 microns, or 5 microns or less.

11. A mixture of crystalline laquinimod sodium particles prepared by the process of claim 8, wherein (i) 90% or more of the total amount by volume of the laquinimod sodium particles have a size of 40 microns or less, and (ii) 50% or more of the total amount by volume of the laquinimod sodium particles have a size of 15 microns or less.

12. A pharmaceutical composition comprising the mixture of claim 11 and a pharmaceutically acceptable carrier.

13. A mixture of crystalline laquinimod sodium particles, wherein (i) 90% or more of the total amount by volume of the laquinimod sodium particles have a size of 40 microns or less and (ii) 50% or more of the total amount by volume of the laquinimod sodium particles have a size of 15 microns or less, and wherein
a) an amount of aluminum in the mixture is less than 5 ppm relative to the amount by weight of laquinimod sodium;
b) an amount of calcium, in the mixture is less than 60 ppm relative to the amount by weight of laquinimod sodium;
c) an amount of copper in the mixture is less than 1 ppm, relative to the amount by weight of laquinimod sodium;
d) an amount of iron in the mixture is less than 4 ppm relative to the amount by weight of laquinimod sodium; or
e) an amount of zinc in the mixture is less than 7 ppm relative to the amount by weight of laquinimod sodium.

14. A pharmaceutical composition comprising the mixture of claim 13 and a pharmaceutically acceptable carrier.

15. The mixture of claim 11, wherein:
a) the mixture has a bulk density of 0.2 g/mL to 0.4 g/mL;
b) the mixture has a tapped density of 0.40 g/mL to 0.7 g/mL;
c) an amount of aluminum in the mixture is less than 5 ppm relative to the amount by weight of laquinimod sodium;
d) an amount of calcium in the mixture is less than 60 ppm relative to the amount by weight of laquinimod sodium;
e) an amount of copper in the mixture is less than 1 ppm relative to the amount by weight of laquinimod sodium;
f) an amount of iron in the mixture is less than 4 ppm relative to the amount by weight of laquinimod sodium;
g) an amount of zinc in the mixture is less than 7 ppm relative to the amount by weight of laquinimod sodium;
h) an amount of heavy metal in the mixture is no more than 0.002% relative to the amount by weight of laquinimod sodium;
i) a total amount of polar impurities in the mixture is no more than 1.00% relative to the amount of laquinimod sodium as measured by HPLC;
j) an amount of 5-chloro-4-hydroxy-1-methyl-2-oxo-1,2-dihydroquinoline (MCQ) in the mixture is no more than 0.15% relative to the amount of laquinimod sodium as measured by HPLC;
k) an amount of 5-chloro-4-hydroxy-1-methyl-2-oxo-1,2-dihydroquinoline-3-carboxylic acid (MCQCA) in the mixture is no more than 0.15% relative to the amount of laquinimod sodium as measured by HPLC;
l) an amount of methyl 5-chloro-4-hydroxy-1-methyl-2-oxo-1,2-dihydroquinoline-3-carboxylate (MCQME) in the mixture is no more than 0.12% relative to the amount of laquinimod sodium as measured by HPLC;
m) an amount of ethyl 5-chloro-4-hydroxy-1-methyl-2-oxo-1,2-dihydroquinoline-3-carboxylate (MCQME) in the mixture is no more than 0.10% relative to the amount of laquinimod sodium as measured by HPLC;
n) a total amount of non-polar impurities in the mixture is no more than 0.50% relative to the amount of laquinimod sodium as measured by HPLC;
o) an amount of N-ethyl aniline in the mixture is no more than 0.10% relative to the amount of laquinimod sodium as measured by HPLC;
p) an amount of laquinimod acid in the mixture o more than 1.00% relative to the amount of laquinimod sodium as measured by HPLC;
q) an amount of dimethyl malonate in the mixture is no more than 0.10% relative to the amount of laquinimod sodium as measured by HPLC;
r) an amount of diethyl malonate in the mixture is no more than 0.10% relative to the amount of laquinimod sodium as measured by HPLC;
s) an amount of dimethyl sulfate more than 1 ppm relative to the amount by weight of laquinimod sodium;
t) an amount of water in the mixture is no more than 1.5% by weight relative to the amount of laquinimod sodium as measured by K.F. coulometric titration;
u) the mixture comprises an amount of sodium from 5.8% to 6.44 relative to the amount weight of laquinimod sodium;

v) an amount of ethanol in the mixture is no more than 5000 ppm relatives to the amount by weight of laquinimod sodium;
w) an amount of n-heptane in the mixture is no more than 5000 ppm relative to the amount by weight of laquinimod sodium;
x) an amount of n-octane in the mixture is no more than 2000 ppm relative to the amount by weight of laquinimod sodium;
y) an amount of methanol in the mixture is no more than 3000 ppm relative to the amount by weight of laquinimod sodium;
z) an amount of acetone in the mixture is no more than 5000 ppm relative to the amount by weight of laquinimod sodium;
aa) an amount of dioxane in the mixture is no more than 380 ppm relative to the amount by weight of laquinimod sodium;
bb) an amount of dimethyl formamide in the mixture is no more than 880 ppm relative to the amount by weight of laquinimod sodium;
cc) an amount of 5-chloro-4-hydroxy-1-methyl-2-oxo-N-phenyl-1,2-dihydroquinoline-3-carboxamide (DELAQ) in the mixture is no more than 0.10% relative to the amount of laquinimod sodium as measured by HPLC; and/or
dd) an amount of N-ethyl-4,5-dihydroxy-1-methyl-2-oxo-N-phenyl-1,2,3,4-tetrahydroquinoline-3-carboxamide (5-HLAQ) in the mixture is no more than 0.10% relative to the amount of laquinimod sodium as measured by HPLC.

16. The mixture of claim 11, wherein:
a) the mixture has a bulk density of 0.2 g/mL to 0.4 g/mL;
b) the mixture has a tapped density of 0.40 g/mL to 0.7 g/mL;
c) an amount of heavy metal in the mixture is no more than 0.002% relative to the amount by weight of laquinimod sodium;
d) a total amount of polar impurities in the mixture is no more than 1.00% relative to the amount of laquinimod sodium as measured by HPLC;
e) an amount of 5-chloro-4-hydroxy-1-methyl-2-oxo-1,2-dihydroquinoline (MCQ) in the mixture is no more than 0.15% relative to the amount of laquinimod sodium as measured by HPLC;
f) an amount of 5-chloro-4-hydroxy-1-methyl-2-oxo-1,2-dihydroquinoline-3-carboxylic acid (MCQCA) in the mixture is no more than 0.15% relative to the amount of laquinimod sodium as measured by HPLC;
g) an amount of methyl 5-chloro-4-hydroxy-1-methyl-2-oxo-1,2-dihydroquinoline-3-carboxylate (MCQME) in the mixture is no more than 0.12% relative to the amount of laquinimod sodium as measured by HPLC;
h) an amount of ethyl 5-chloro-4-hydroxy-1-methyl-2-oxo-1,2-dihydroquinoline-3-carboxylate (MCQME) in the mixture is no more than 0.10% relative to the amount of laquinimod sodium as measured by HPLC;
i) a total amount of non-polar impurities in the mixture s no more than 0.50% relative to the amount of laquinimod sodium as measured by HPLC;
j) an amount of N-ethyl aniline in the mixture is no more than 0.10% relative to the amount of laquinimod sodium as measured by HPLC;
k) an amount of laquinimod acid in the mixture is no more than 1.00% relative to the amount of laquinimod sodium as measured by HPLC;
l) an amount of dimethyl malonate in the mixture is no more than 0.10% relative to the amount of laquinimod sodium as measured by HPLC;
m) an amount of diethyl malonate in the mixture is no more than 0.10% relative to the amount of laquinimod sodium as measured by HPLC;
n) an amount of dimethyl sulfate in the mixture is no more than 1 ppm relative to the amount by weight of laquinimod sodium;
o) an amount of water in the mixture is no more than 1.5% by weight relative to the amount of laquinimod sodium as measured by K.F. coulometric titration;
p) the mixture comprises an amount of sodium from 5.8% to 6.4% relative to the amount by weight of laquinimod sodium;
q) an amount of ethanol in the mixture is no more than 5000 ppm relative to the amount by weight of laquinimod sodium;
r) an amount of n-heptane in the mixture is no more than 5000 ppm relative to the amount by weight of laquinimod sodium;
s) an amount of n-octane in the mixture is no more than 2000 ppm relative to the amount by weight of laquinimod sodium;
t) an amount of methanol in the mixture is no more than 3000 ppm relative to the amount by weight of laquinimod sodium;
u) an amount of acetone in the mixture is no more than 5000 ppm relative to the amount by weight of laquinimod sodium;
v) an amount of dioxane in the mixture is no more than 380 ppm relative to the amount by weight of laquinimod sodium;
w) an amount of dimethyl formamide in the mixture is no more than 880 ppm relative to the amount by weight of laquinimod sodium;
x) an amount of 5-chloro-4-hydroxy-1-methyl-2-oxo-N-phenyl-1,2-dihydroquinoline-3-carboxamide (DELAQ) in the mixture is no more than 0.10% relative to the amount of laquinimod sodium as measured by HPLC; and
y) an amount of N-ethyl-4,5-dihydroxy-1-methyl-2-oxo-N-phenyl-1,2,3,4-tetrahydroquinoline-3-carboxamide (5-HLAQ) in the mixture is no more than 0.10% relative to the amount of laquinimod sodium as measured by HPLC.

17. The pharmaceutical composition of claim 12, wherein:
a) a total amount of 5-chloro-4-hydroxy-1-methyl-2-oxo-1,2-dihydroquinoline (MCQ) and 5-chloro-4-hydroxy-1-methyl-2-oxo-1,2-dihydroquinoline-3-carboxylic acid (MCQCA) in the pharmaceutical composition is no more than 0.50% relative to the amount of laquinimod sodium as measured by HPLC;
b) a total amount of polar impurities in the pharmaceutical composition is no more than 2.00% relative to the amount of laquinimod sodium as measured by HPLC;
c) an amount of N-ethyl aniline in the pharmaceutical composition is no more than 0.50% relative to the amount of laquinimod sodium as measured by HPLC;
d) a total amount of non-polar impurities in the pharmaceutical composition is no more than 1.00% relative to the amount of laquinimod sodium as measured by HPLC;
e) an amount of water in the pharmaceutical composition is no more than 0.80% relative to the amount of laquinimod sodium as measured by K.F. coulometric titration;

f) the pharmaceutical composition comprises an amount of sodium from 5.3% to 6.4% relative to the amount by weight of laquinimod sodium;
g) an amount of ethanol in the pharmaceutical composition is no more than 5000 ppm relative to the amount by weight of laquinimod sodium;
h) an amount of n-heptane in the pharmaceutical composition is no more than 5000 ppm relative to the amount by weight of laquinimod sodium;
i) an amount of n-octane in the pharmaceutical composition is no more than 2000 ppm relative to the amount by weight of laquinimod sodium;
j) an amount of methanol in the pharmaceutical composition is no more than 3000 ppm relative to the amount by weight of laquinimod sodium;
k) an amount of acetone in the pharmaceutical composition is no more than 5000 ppm relative to the amount by weight of laquinimod sodium;
l) an amount of dioxane in the pharmaceutical composition is no more than 380 ppm relative to the amount by weight of laquinimod sodium;
m) an amount of dimethyl formamide in the pharmaceutical composition is no more than 880 ppm relative to the amount by weight of laquinimod sodium;
n) an amount of N-ethyl-4,5-dihydroxy-1-methyl-2-oxo-N-phenyl-1,2,3,4-tetrahydroquinoline-3-carboxamide (5-HLAQ) in the mixture is no more than 0.50% relative to the amount of laquinimod sodium as measured by HPLC;
o) an amount of 5-chloro-N-ethyl-3-hydroxy-1-methyl-5-2,4-dioxo-N-phenyl-1,2,3,4-tetrahydroquinoline-3-carboxamide (3-HLAQ) in the pharmaceutical composition is no more than 0.50% relative to the amount of laquinimod sodium as measured by HPLC;
p) an amount or N-ethyl-4-hydroxy-1-methyl-5-(methyl (2,3,4,5,6-pentahydroxyhexyl)amino)-2-oxo-N-phenyl-1,2-dihydroquinoline-3-carboxamide (MEG-LAQ) in the pharmaceutical composition is no more than 1.00% relative to the amount of laquinimod sodium as measured by HPLC; and/or
q) an amount of water in the pharmaceutical composition is no more than 1.50% relative to the amount of laquinimod sodium as measured by K.F. coulometric titration.

18. The pharmaceutical composition of claim 12, comprising:
a) a total amount of 5-chloro-4-hydroxy-1-methyl-2-oxo-1,2-dihydroquinoline (MCQ) and 5-chloro-4-hydroxy-1-methyl-2-oxo-1,2-dihydroquinoline-3-carboxylic acid (MCQCA) in the pharmaceutical composition is no more than 0.50% relative to the amount of laquinimod sodium as measured by HPLC;
b) a total amount of polar impurities in the pharmaceutical composition is no more than 2.00% relative to the amount of laquinimod sodium as measured by HPLC;
c) an amount of N-ethyl aniline in the pharmaceutical composition is no more than 0.50% relative to the amount of laquinimod sodium as measured by HPLC;
d) a total amount of non-polar impurities in the pharmaceutical composition is no more than 1.00% relative to the amount of laquinimod sodium as measured by HPLC;
e) an amount of water in the pharmaceutical composition is no more than 0.80% relative to the amount of laquinimod sodium as measured by K.F. coulometric titration or an amount of water in the pharmaceutical composition is no more than 1.50% relative to the amount of laquinimod sodium as measured by K.F. coulometric titration;
f) an amount of ethanol in the pharmaceutical composition is no more than 5000 ppm relative to the amount by weight of laquinimod sodium;
g) an amount of n-heptane in the pharmaceutical composition is no more than 5000 ppm relative to the amount by weight of laquinimod sodium;
h) an amount of n-octane in the pharmaceutical composition is no more than 2000 ppm relative to the amount by weight of laquinimod sodium;
i) an amount of methanol in the pharmaceutical composition is no more than 380 ppm relative to the amount by we of laquinimod sodium;
j) an amount of acetone in the pharmaceutical composition is no more than 880 ppm relative to the amount by weight of laquinimod sodium;
k) an amount of dioxane in the pharmaceutical composition is no more than 380 ppm relative to the amount by weight of laquinimod sodium;
l) an amount of dimethyl formamide in the pharmaceutical composition is no more than 880 ppm relative to the amount by weight of laquinimod sodium;
m) an amount of N-ethyl-4,5-dihydroxy-1-methyl-2-oxo-N-phenyl-1,2,3,4-tetrahydroquinoline-3-carboxamide (5-HLAQ) in the mixture is no more than 0.50% relative to the amount of laquinimod sodium as measured by HPLC;
n) an amount of 5-chloro-N-ethyl-3-hydroxy-1-methyl-5-2,4-dioxo-N-phenyl-1,2,3,4-tetrahydroquinoline-3-carboxamide (3-HLAQ) in the pharmaceutical composition is no more than 0.50% relative to the amount of laquinimod sodium as measured by HPLC; and
o) an amount of N-ethyl-4-hydroxy-1-methyl-5-(methyl (2,3,4,5,6-pentahydroxyhexyl)amino)-2-oxo-N-phenyl-1,2-dihydroquinoline-3-carboxamide (MEG-LAQ) in the pharmaceutical composition is no more than 1.00% relative to the amount of laquinimod sodium as measured by HPLC.

19. The mixture of claim 1, wherein
a) the mixture has a bulk density of 0.2 g/mL to 0.4 g/mL;
b) the mixture has a tapped density of 0.4 g/mL to 0.7 g/mL;
c) an amount of ethyl 5-chloro-4-hydroxy-1-methyl-2-oxo-1,2-dihydroquinoline-3-carboxylate (NCQEE) in the mixture is no more than 0.10% relative to the amount of laquinimod sodium as measured by HPLC,
d) a total amount of polar impurities in the mixture is no more than 1.00% relative to the amount of laquinimod sodium as measured by HPLC,
e) a total amount of non-polar impurities in the mixture is no more than 0.50% relative to the amount of laquinimod sodium as measured by HPLC,
f) an amount of N-ethyl aniline in the mixture is no more than 0.10% relative to the amount of laquinimod sodium as measured by HPLC,
g) an amount of N-ethyl-4,5-dihydroxy-1-methyl-2-oxo-N-phenyl-1,2,3,4-tetrahydroquinoline-3-carboxamide (5-HLAQ) in the mixture is no more than 0.10% relative to the amount of laquinimod sodium as measured by HPLC,
h) an amount of 5-chloro-4-hydroxy-1-methyl-2-oxo-N-phenyl-1,2-dihydroquinoline-3-carboxamide (DELAQ) in the mixture is no more than 0.10% relative to the amount of laquinimod sodium as measured by HPLC, i) an amount of laquinimod acid in the mixture is no more than 1.00% relative to the amount of laquinimod sodium as measured by HPLC,
j) an amount of diethyl malonate in the mixture is no more than 0.10% relative to the amount of laquinimod sodium as measured by HPLC,
k) an amount of dimethyl malonate in the mixture is no more than 0.10% relative to the amount of laquinimod sodium as measured by HPLC,
l) an amount of dimethyl sulfate in the mixture is no more than 1 ppm relative to the amount by weight of laquinimod sodium,
m) an amount of water in the mixture is no more than 1.5% by weight relative to the amount of laquinimod sodium as measured by K.F. coulometric titration,
n) an amount of sodium from 5.8% to 6.4% relative to the amount by weight of laquinimod sodium,
o) an amount of ethanol in the mixture is no more than 5000 ppm relative to the amount by weight of laquinimod sodium,
p) an amount of n-heptane in the mixture is no more than 5000 ppm relative to the amount by weight of laquinimod sodium,
q) an amount of n-octane in the mixture is no more than 2000 ppm relative to the amount by weight of laquinimod sodium,
r) an amount of methanol in the mixture is no more than 3000 ppm relative to the amount by weight of laquinimod sodium,
s) an amount of acetone in the mixture is no more than 5000 ppm relative to the amount by weight of laquinimod sodium,
t) an amount of dioxane in the mixture is no more than 380 ppm relative to the amount by weight of laquinimod sodium, and
u) an amount of dimethyl formamide in the mixture is no more than 880 ppm relative to the amount by weight of laquinimod sodium.

20. The pharmaceutical composition of claim 5, wherein
a) a total amount of 5-chloro-4-hydroxy-1-methyl-2-oxo-1,2-dihydroquinoline (MCQ) and 5-chloro-4-hydroxy-1-methyl-2-oxo-1,2-dihydroquinoline-3-carboxylic acid (MCQCA) in the pharmaceutical composition is no more than 0.50% relative to the amount of laquinimod sodium as measured by HPLC,
b) a total amount of 5-HLAQ is no more than 0.50% relative to the amount of laquinimod sodium as measured by HPLC,
c) a total amount of polar impurities in the pharmaceutical composition is no more than 2.00% relative to the amount of laquinimod sodium as measured by HPLC,
d) an amount of N-ethyl aniline in the pharmaceutical composition is no more than 0.50% relative to the amount of laquinimod sodium as measured by HPLC,
e) an amount of 5-chloro-N-ethyl-3-hydroxy-1-methyl-5-2,4-dioxo-N-phenyl-1,2,3,4-tetrahydroquinoline-3-carboxamide (3-HLAQ) in the pharmaceutical composition is no more than 0.50% relative to the amount of laquinimod sodium as measured by HPLC,
f) a total amount of non-polar impurities in the pharmaceutical composition is no more than 1.00% relative to the amount of laquinimod sodium as measured by HPLC,
g) an amount of N-ethyl-4-hydroxy-1-methyl-5-(methyl (2,3,4,5,6-pentahydroxyhexyl)amino)-2-oxo-N-phenyl-1,2-dihydroquinoline-3-carboxamide (MEG-LAQ) in the pharmaceutical composition is no more than 1.00% relative to the amount of laquinimod sodium as measured by HPLC,
h) an amount of water in the pharmaceutical composition is no more than 1.50% relative to the amount of laquinimod sodium as measured by K.F. coulometric titration, or an amount of water in the pharmaceutical composition is no more than 0.80% relative to the amount of laquinimod sodium as measured by K.F. coulometric titration
i) an amount of ethanol in the pharmaceutical composition is no more than 5000 ppm relative to the amount by weight of laquinimod sodium,
j) an amount of n-heptane in the pharmaceutical composition is no more than 5000 ppm relative to the amount by weight of laquinimod sodium,
k) an amount of n-octane in the pharmaceutical composition is no more than 2000 ppm relative to the amount by weight of laquinimod sodium,
l) an amount of methanol in the pharmaceutical composition is no more than 3000 ppm relative to the amount by weight of laquinimod sodium,
m) an amount of acetone in the pharmaceutical composition is no more than 5000 ppm relative to the amount by weight of laquinimod sodium,
n) an amount of dioxane in the pharmaceutical composition is no more than 380 ppm relative to the amount by weight of laquinimod sodium, and
o) an amount of dimethyl formamide in the pharmaceutical composition is no more than 880 ppm relative to the amount by weight of laquinimod sodium.

21. The process of claim 8, wherein the isolated recrystallized laquinimod sodium in step d) is a mixture of crystalline laquinimod sodium particles having a particle size distribution such that (i) 90% or more of the total amount by volume of the laquinimod sodium particles have a size of 40 microns or less, and (ii) 50% or more of the total amount by volume of the laquinimod sodium particles have a size of 15 microns or less.

22. The mixture of claim 11, wherein (i) 90% or more of the total amount by volume of the laquinimod sodium particles have a size of 40 microns or less, (ii) 50% or more of the total amount by volume of the laquinimod sodium particles have a size of 15 microns or less, and (iii) 10% or more of the total amount by volume of the laquinimod sodium particles have u size of 5 microns or less.

\* \* \* \* \*